US008353813B2

(12) United States Patent
Shaknovich

(10) Patent No.: US 8,353,813 B2
(45) Date of Patent: Jan. 15, 2013

(54) SYSTEM AND METHOD FOR ASSISTED PARTITIONING OF BODY CONDUITS

(76) Inventor: Alexander Shaknovich, White Plains, NY (US)

( * ) Notice: Subject to any disclaimer, the term of this patent is extended or adjusted under 35 U.S.C. 154(b) by 569 days.

(21) Appl. No.: 11/733,862

(22) Filed: Apr. 11, 2007

(65) Prior Publication Data

US 2008/0071135 A1 Mar. 20, 2008

Related U.S. Application Data

(63) Continuation of application No. PCT/US2005/036706, filed on Oct. 12, 2005.

(60) Provisional application No. 60/618,010, filed on Oct. 12, 2004.

(51) Int. Cl.
 *A61M 1/12* (2006.01)
(52) U.S. Cl. ............ 600/17; 623/1.15; 600/486
(58) Field of Classification Search .......... 600/16–19, 600/486, 505; 607/2, 6, 17; 623/1.15
See application file for complete search history.

(56) References Cited

U.S. PATENT DOCUMENTS

| | | | | |
|---|---|---|---|---|
| 4,621,646 A | * | 11/1986 | Bryant | 600/505 |
| 4,958,630 A | * | 9/1990 | Rosenbluth et al. | 600/40 |
| 5,709,539 A | * | 1/1998 | Hammer et al. | 417/477.3 |
| 7,614,998 B2 | * | 11/2009 | Gross et al. | 600/17 |
| 2002/0040178 A1 | | 4/2002 | Sayet et al. | |
| 2003/0191527 A1 | | 10/2003 | Shaknovich | |

FOREIGN PATENT DOCUMENTS

| | | |
|---|---|---|
| WO | WO9857599 | 12/1998 |
| WO | WO0048531 | 8/2000 |
| WO | WO0217819 | 3/2002 |

* cited by examiner

*Primary Examiner* — Carl H Layno
*Assistant Examiner* — Pamela M Bays
(74) *Attorney, Agent, or Firm* — Baker Botts L.L.P.

(57) ABSTRACT

A treatment strategy for treatment of elevated pressure in a body conduit, such as a pulmonary vein, with a prosthetic partitioning device for placement in and/or about pulmonary veins is described, as well as delivery systems, and strategies for use thereof. A control device is configured to transmit signals to the prosthetic device to effectuate the repetitive transition between a first, less restricted flow configuration and a second, restricted flow configuration are described. A sensor device may be provided for monitoring physiological parameters of the patient, and can provide signals to the control device for effectuating the transition between the first and second configuration.

21 Claims, 15 Drawing Sheets

SYSTEM AND METHOD FOR ASSISTED PARTITIONING OF BODY CONDUITS

CROSS-REFERENCE TO RELATED APPLICATIONS

This application is a continuation of International Application PCT/US05/036706, filed Oct. 12, 2005, which claims the benefit of U.S. Provisional Patent Application Ser. No. 60/618,010, filed Oct. 12, 2004, entitled "System and Method For Assisted Partitioning of Body Conduits," each of which is incorporated by reference herein in its entirety.

BACKGROUND

1. Field of the Invention

The present invention relates generally to the field of systems and methods for partitioning body conduits with a class of prosthetic partitioning devices, specifically with prosthetic devices for placement in and/or about pulmonary vein(s) for the purpose of treating congestive heart failure, to procedures for installing same.

2. Background of the Invention

Congestive heart failure is a complex syndrome of various etiologies associated, in some patients, with abnormally high pulmonary venous pressures at rest and/or in conjunction with physical, emotional or metabolic stress. Congestive heart failure is a major cause of cardiovascular morbidity and mortality, affecting tens of millions of patients worldwide. Current treatment of chronic congestive heart failure often relies on life-long medical therapy if congestive heart failure persists after correction of all reversible causes of congestive heart failure.

As illustrated in FIG. 1, the left atrium LA of the human heart H receives oxygenated blood from the lungs (not shown) through the pulmonary veins PV (the right and left superior and inferior pulmonary veins), and delivers it through the mitral MV to the left ventricle LV. Contraction of the left ventricle LV pumps the oxygenated blood across the aortic valve AV into the high pressure, high resistance systemic circulation through the aorta A, and out to the rest of the body (See general flow direction as indicated by arrow F in FIG. 1).

For the purposes of illustration, the anatomy of central larger pulmonary veins is compared with anatomy of larger veins in the lower extremities in humans. Certain larger veins in the lower extremities of human beings normally have valves that, under conditions of normal function, permit movement of blood largely only toward the heart. In effect, properly functioning venous valves in the lower extremities protect, or partition, the veins of the lower extremities from the relatively high hydrostatic pressure of the column of venous blood between the right atrium RA and the lower extremities due to the effect of gravity during upright posture. Thus, normally, when upright posture is assumed, venous blood pressure in the foot is predominantly less than the sum of relatively low pressure in the right atrium RA and relatively high hydrostatic pressure of the column of venous blood between the right atrium RA and the foot due to the effect of gravity. When these venous valves in the lower extremities are incompetent, venous blood pressure in the foot becomes predominantly equal to the sum of the relatively low pressure in the right atrium RA and relatively high hydrostatic pressure of the column of venous blood between the right atrium RA and the foot, often resulting in pathologic dilatation of the veins in the lower extremities and/or edema.

The pulmonary veins PV, which drain into the left atrium LA, are not known to have directional valves in humans or other mammals. Under normal conditions, the pressure in the pulmonary veins PV is, with a phase shift dependent on the distance from the left atrium LA, essentially the same as or slightly higher than the pressure in the left atrium LA. Thus, protection, or partitioning, of the pulmonary veins PV from the high systolic pressure of the contracting left ventricle LV, is the same as the protection of the left atrium LA. Such protection is entirely and solely due to proper function of the mitral valve MV. An example of abnormal function of the mitral valve MV is mitral regurgitation, in which insufficient closure of the mitral valve MV allows the systolic flow of blood from the left ventricle LV into the left atrium LA. The mitral regurgitation may occur due to damage or malfunction of the mitral valve leaflets, and/or the mitral annulus, and/or the chordae tendineae, and/or the papillary muscles, and/or dilatation of the left ventricle LV. During systole, the impaired partitioning of the left ventricle LV from the left atrium LV, and therefore from the pulmonary veins PV, transmits relatively high left ventricular systolic pressure, with a phase shift, into the pulmonary veins PV, which often results in marked elevation of the mean pulmonary venous pressure PV, and leading to pulmonary edema and congestive heart failure. Another example of abnormal function of the mitral valve MV is mitral stenosis. In mitral stenosis, opening of the mitral valve MV in diastole and the normal diastolic blood flow from the left atrium LA into the left ventricle LV are compromised due to damage or malfunction of the mitral valve leaflets and chordae tendineae, and occur only at markedly elevated diastolic, and therefore mean, pressure in the left atrium LA. This elevated pressure is transmitted, with a phase shift, into the pulmonary veins PV, resulting in marked elevation of the mean pulmonary venous pressure PV. In patients with mitral stenosis (despite typically normal systolic function of the mitral valve MV providing effective systolic partitioning between the left ventricle LV and left atrium LA, and therefore pulmonary veins PV), signs and symptoms of congestive heart failure may develop due to markedly elevated diastolic, and therefore mean, pressure in the left atrium LA, and therefore pulmonary veins PV.

Treatment of congestive heart failure largely due to mitral regurgitation is typically often performed by surgical replacement of the mitral valve with a prosthetic valve. In a substantial number of patients, surgical replacement of a regurgitant mitral valve is not possible, or is associated with unacceptable high morbidity and/or mortality.

In other patients, the left ventricle LV may become non-compliant, or stiff, due to a variety of conditions such as, but not limited to, ischemic heart disease, hypertension, aortic stenosis, diabetes mellitus, or aging. The transfer of blood into a left ventricle LV having decreased compliance during diastole can only be effected when the left atrial, and therefore pulmonary venous, diastolic pressure is markedly elevated. In such patients, despite typically normal function of the mitral valve providing effective systolic partitioning between the left ventricle LV and left atrium LA, and therefore pulmonary veins PV, signs and symptoms of congestive heart failure may develop due to markedly elevated diastolic, and therefore mean, pressure in the left atrium LA, and therefore pulmonary veins PV. At present, congestive heart failure due to diastolic left ventricular dysfunction can only be treated with medications, with variable efficacy.

Accordingly, there is a need for a system that provides effective partitioning of the left atrium and pulmonary veins without the need for medications or valve replacement therapies.

SUMMARY OF THE INVENTION

A system for partitioning the flow in a body conduit of a patient is provided comprising a prosthetic partitioning device configured for coaxial attachment to a body conduit and movable between a first configuration permitting a less restricted fluid flow therethrough and a second configuration permitting a more restricted fluid flow therethrough; a control device configured to transmit signals to the prosthetic partitioning device to effectuate the repetitive transition between the first configuration and the second configuration, e.g., from the first configuration to the second configuration and the second configuration to the first configuration. The signal transmitted to the prosthetic partitioning device may be an electrical signal, or a signal implicitly transmitted to the partitioning device by the transmission of an expansion medium, a hydraulic medium, or a pneumatic medium, as appropriate, to the mechanism for transitioning the prosthetic partitioning device between the first configuration and second configuration.

In an exemplary embodiment of the invention, the system includes a sensor device for monitoring certain characteristics or physiological parameters of the patient, such as heart rate, hemodynamic characteristics or pressure characteristics. The control device may be configured to receive signals from the sensor device and to transmit signals to the prosthetic partitioning device to effectuate the repetitive transition between the first configuration and the second configuration. The term "coaxial attachment" shall be understood to refer to the placement of the prosthetic partitioning device on the exterior of the body conduit, or alternatively, for placement within the interior of the body conduit. The prosthetic partitioning device may comprise an expandable or contractible component, such as an expandable balloon. The prosthetic partitioning device may be actuated to move between the first configuration and the second configuration by pneumatic, hydraulic, electric, electromechanical, magnetic, chemical means, or by the use of an autologous transplant of skeletal muscle.

According to an exemplary embodiment, the prosthetic partitioning device is installed on a pulmonary vein. Alternatively, a plurality of the prosthetic partitioning devices may be installed on a pulmonary vein.

The control device may be configured to effectuate the repetitive transition between the first configuration and the second configuration during a predetermined time period. For example, the control device may be configured to activate the prosthetic partitioning device only at night. The control device may activate all or some of the prosthetic partitioning devices during all cardiac cycles or particular cardiac cycles, or when predetermined heart rate or hemodynamic criteria are met.

The system may be configured such that the prosthetic partitioning device is configured to remain in the first configuration in the event of a malfunction of the system, i.e., to allow unrestricted flow through the body conduit when the prosthetic partitioning device is unable to properly effectuate the repetitive transition between the first configuration and the second configuration. For example, if the prosthetic partitioning device includes an expandable balloon structure, it is configured to remain in an uninflated configuration which allows flow therethrough in the event of a malfunction of the system.

A method for partitioning the flow in a body conduit of a patient is also disclosed comprising providing a prosthetic partitioning device coaxially attached to a body conduit and movable between a first configuration permitting a less restricted fluid flow therethrough and a second configuration permitting a more restricted fluid flow therethrough; and transmitting signals to the prosthetic partitioning device to effectuate the transition from the first configuration to the second configuration.

In an exemplary embodiment, the method may include monitoring the characteristics or physiological parameters of the patient, including monitoring the cardiac electrical activity in the patient's right atrium, left atrium, or both atria, and the right ventricle, left ventricle, or both ventricles. In another embodiment, monitoring the activity of the patient comprises monitoring the pressure of fluid in the patient's left atrium, left ventricle, or both.

A delivery system for delivery of a prosthetic partitioning device for partitioning the flow in a body conduit of a patient is also provided, comprising a prosthetic partitioning device configured for coaxial attachment to a body conduit and movable between a first configuration permitting a less restricted fluid flow therethrough and a second configuration permitting a more restricted fluid flow therethrough, the prosthetic partitioning device effectuating transition between the first configuration and the second configuration in response to activity of the patient's body; an elongated catheter configured for insertion into the body conduit having a prosthetic conduit-carrying portion; and a protective sheath configured to cover the prosthetic partitioning device during insertion into the body conduit.

According to an exemplary embodiment, the prosthetic partitioning device is configured for placement on the exterior of the body conduit. In another embodiment, the prosthetic partitioning device is configured for placement within the interior of the body conduit.

The delivery of the prosthetic partitioning device may be performed through open surgical procedures, laparoscopically or by other minimally invasive procedures, or percutaneously.

In accordance with the invention, the object of providing a system for partitioning the left atrium and the pulmonary vein has been met. Further features of the invention, its nature and various advantages will be apparent from the accompanying drawings and the following detailed description of illustrative embodiments.

DESCRIPTION OF THE PREFERRED EMBODIMENTS

This invention will be further understood in view of the following detailed description of exemplary embodiments.

Figure 1:
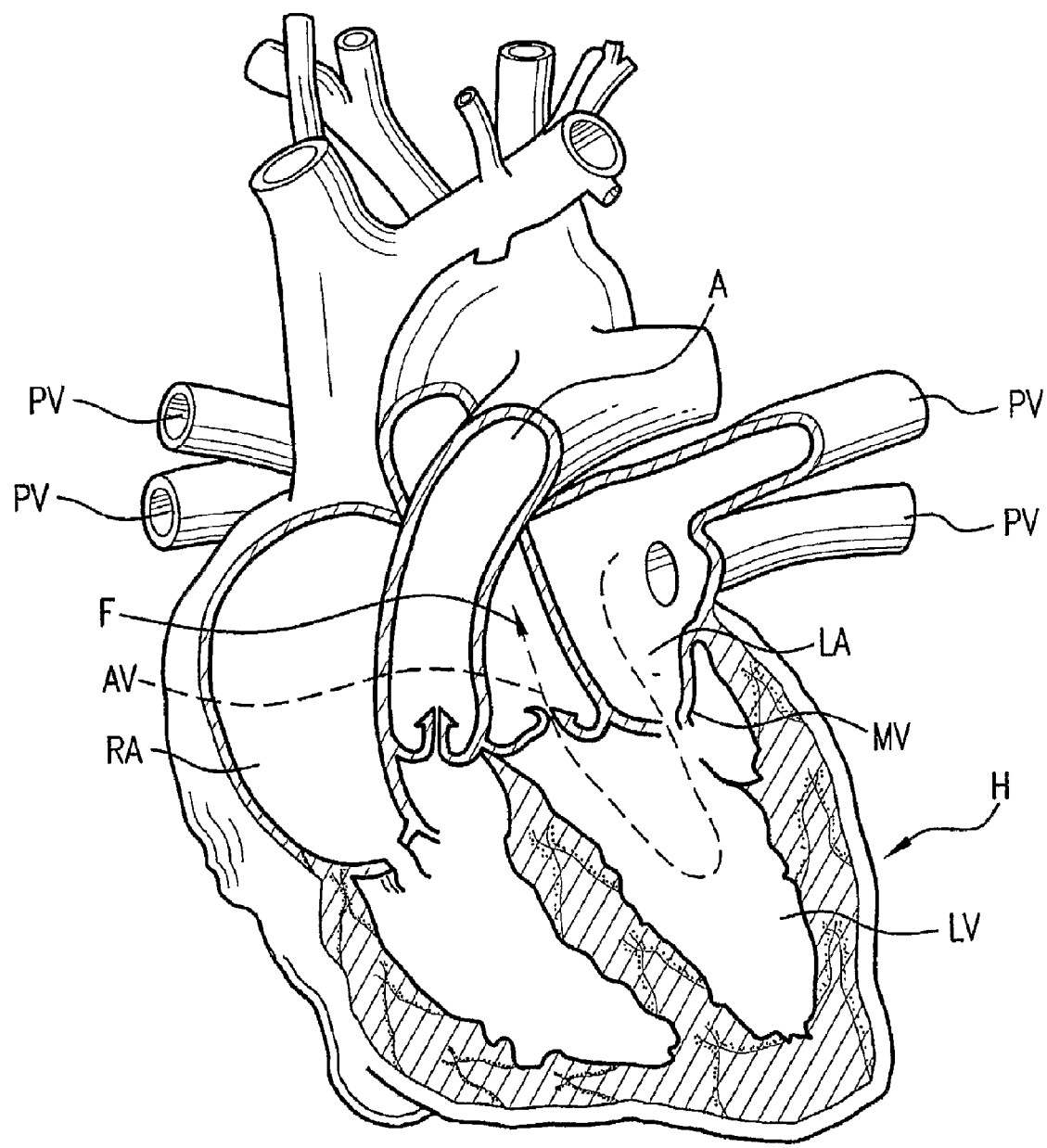
FIG. 1 is a simplified view, in section, of the human heart.
Figure 2:
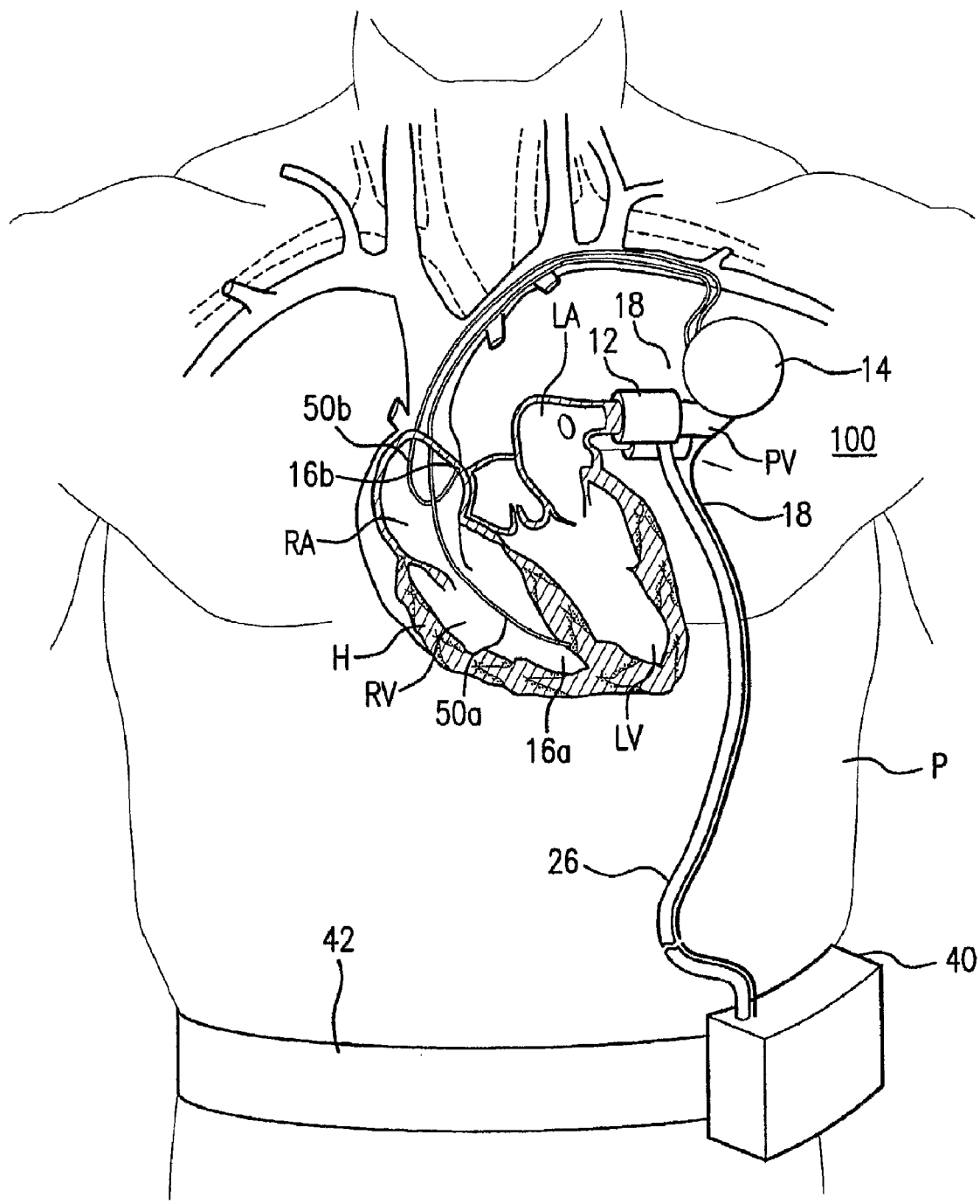
FIG. 2 is a simplified schematic view of a system installed in a patient in accordance with the present invention.

A system in accordance with an exemplary embodiment of the invention provides effective partitioning between body conduits is illustrated in FIG. 2, and generally designated system 100. This system implanted in patient P finds particularly useful application in providing effective partitioning between the left atrium LA of the patient's heart H and one of more of the four pulmonary veins PV for the purpose of lowering mean pulmonary venous pressure, and therefore treatment of conditions such as, e.g., congestive heart failure. Alternatively, the system is useful for treating physiological parameters, e.g., elevated pulmonary venous pressures, independently from physical conditions. Additional methods for partitioning the left atrium from the pulmonary veins is disclosed in U.S. Pat. No. 6,572,652, which is hereby incorporated by reference in its entirety herein.

The system described herein finds application in other blood vessels, such as the vena cava. Systolic vena caval partitioning may useful for providing palliation of tricuspid regurgitation, especially when pulmonary hypertension is present. Assisted partitioning may be useful for prevention of chronic venous engorgement and dilatation, and high cardiac output congestive heart failure due to left-to-right shunting, in hemodialysis arterio-venous fistulae. ECG triggered partitioning could allow flow only during a brief portion of left ventricular diastole, when systemic arterial pressure is at its nadir. Moreover, it is understood that the partitioning strategy may be useful in treating vesiculo-ureteral reflux, with the partitioning device being activated by pressure sensors in the bladder or electrodes in the bladder wall.

As illustrated in FIG. 2, the system 100 includes an prosthetic partitioning device 12 positioned at the body conduit to be effectively partitioned, a control device 14 for actuating the prosthetic partitioning device 12, and a sensor device 16 (16a/16b). In the exemplary embodiment, the prosthetic partitioning device 12 is coaxially positioned at the pulmonary vein PV to partition flow therethrough between the left atrium LA and the pulmonary vein PV. As the term is used herein, partitioning shall refer to restriction of the flow through the body conduit. Restriction of flow may be partial or complete, and is effective in dampening transmission of pressure via the body conduit, in this case, from the left atrium into the more distal pulmonary vein. As discussed herein, coaxial attachment at or about the body conduit shall refer to a prosthetic partitioning device located about the exterior of the body conduit, or within the body conduit. In the exemplary embodiment, there may be four total prosthetic partitioning devices, i.e., one prosthetic partitioning device for each of the four pulmonary veins PV (two are illustrated in FIG. 2). In another embodiment, there may be fewer than one prosthetic partitioning device for each pulmonary vein PV or other body conduit, i.e., three or fewer total. In a further embodiment, two or more prosthetic partitioning devices may be implanted for each pulmonary vein PV or other body conduit. In yet another embodiment, a single prosthetic partitioning device may be provided having the capability to partition two or more pulmonary veins PV or other body conduits.

Figure 3:
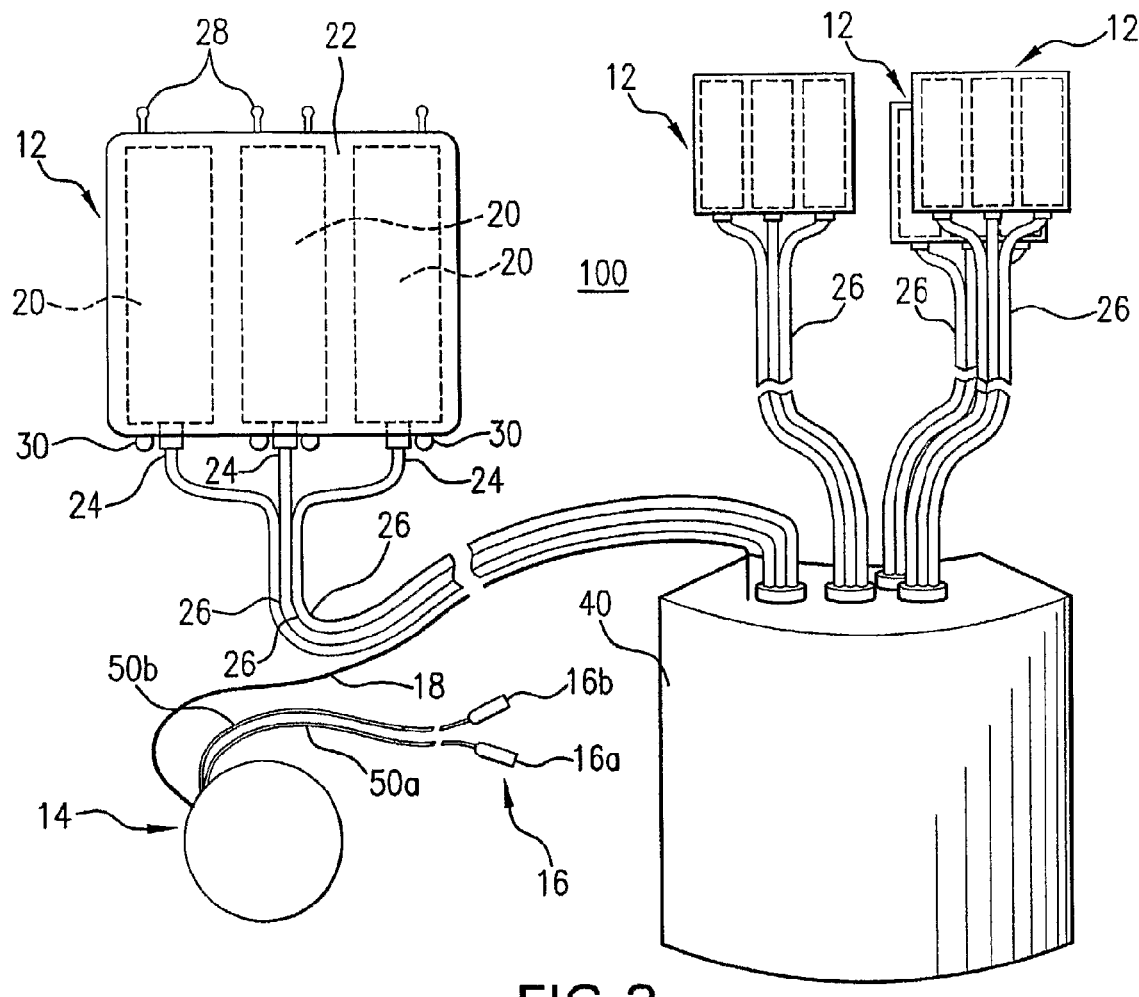
FIG. 3 is a view of the system illustrated in FIG. 2, in accordance with the present invention.

An exemplary embodiment of the system, i.e., system 100, is further illustrated in FIG. 3 (not to scale). In accordance with an exemplary embodiment, prosthetic partitioning device 12 includes a structure that permits coaxial attachment to the body conduit, e.g., the pulmonary vein PV. The prosthetic partitioning device 12 may be activated by the control device 14, as described herein. As will be further described herein, the prosthetic partitioning device 12, is repetitively transitioned between a first configuration, which allows substantially unrestricted flow (or less restricted flow, or in certain embodiments, facilitated flow) of fluid, e.g., blood, to a second configuration, which restricts the flow of fluid therethrough, as discussed above.

Figure 4:
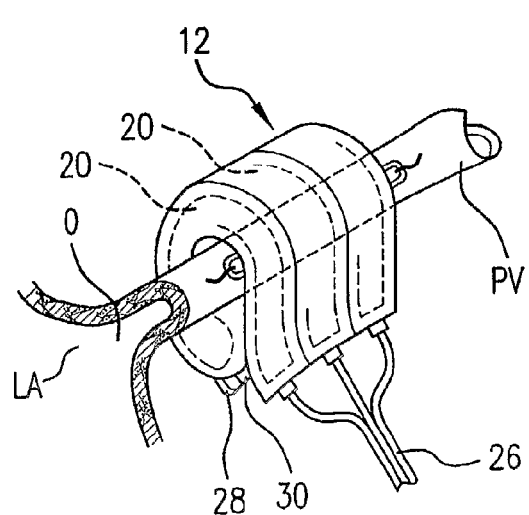
FIG. 4 is a view, in partial section, of the prosthetic partitioning device installed about a patient's body conduit, in accordance with the present invention.

System 100 may include one or more inflatable balloon device(s) 20. (In the exemplary embodiment illustrated in FIG. 3, three balloon devices 20 are illustrated.) The balloon devices may be covered by a flexible sheath 22. Each balloon 20 may be supplied with gas, such as helium, carbon dioxide, or fluid, such as saline, etc., through port 24 by a supply line 26. If there is one balloon 20, or alternatively, if multiple balloons are inflated simultaneously, a single port 24 and supply line 26 may be provided. As illustrated in FIG. 4, the prosthetic partitioning device 12 may be wrapped around the pulmonary vein PV or other body conduit and secured by the use of hooks 28 and loops 30, or alternatively by sutures, clips, or stents, as is known in the art.

With continued reference to FIG. 3, the gas or fluid supplied to balloon(s) 20 via supply line(s) 26 is provided by a pump, such as external pump 40. Such pumps are widely known in the art for use with such devices as left ventricular assist pumps. In accordance with the invention, pump 40 supplies gas or fluid to assist the balloons 20 (rather than blood, as in the ventricular assist pumps.) As illustrated in FIG. 2, the external pump 40 may be worn about the patient's waist by use of a securing strap or belt 42. Alternatively, pump may be implanted in the patient P, and supplied with an external or internal power supply.

Figure 5:
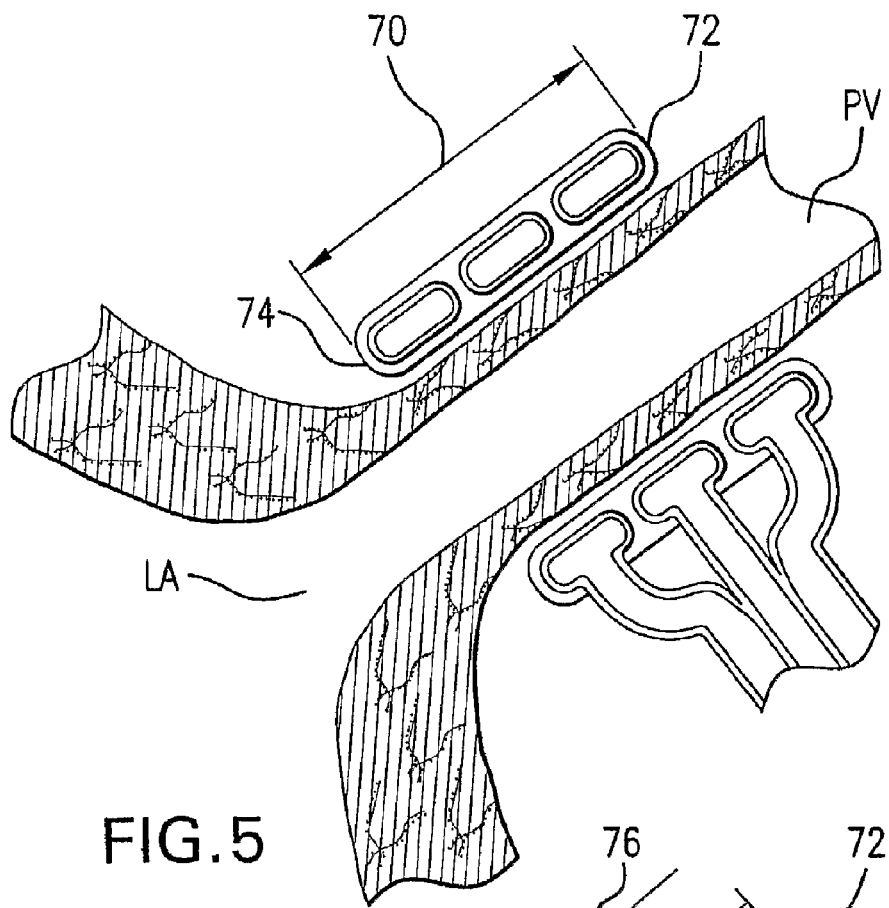
FIG. 5 is a sectional view of the prosthetic partitioning device in a first, less restricted flow configuration, in accordance with the present invention.
Figure 6:
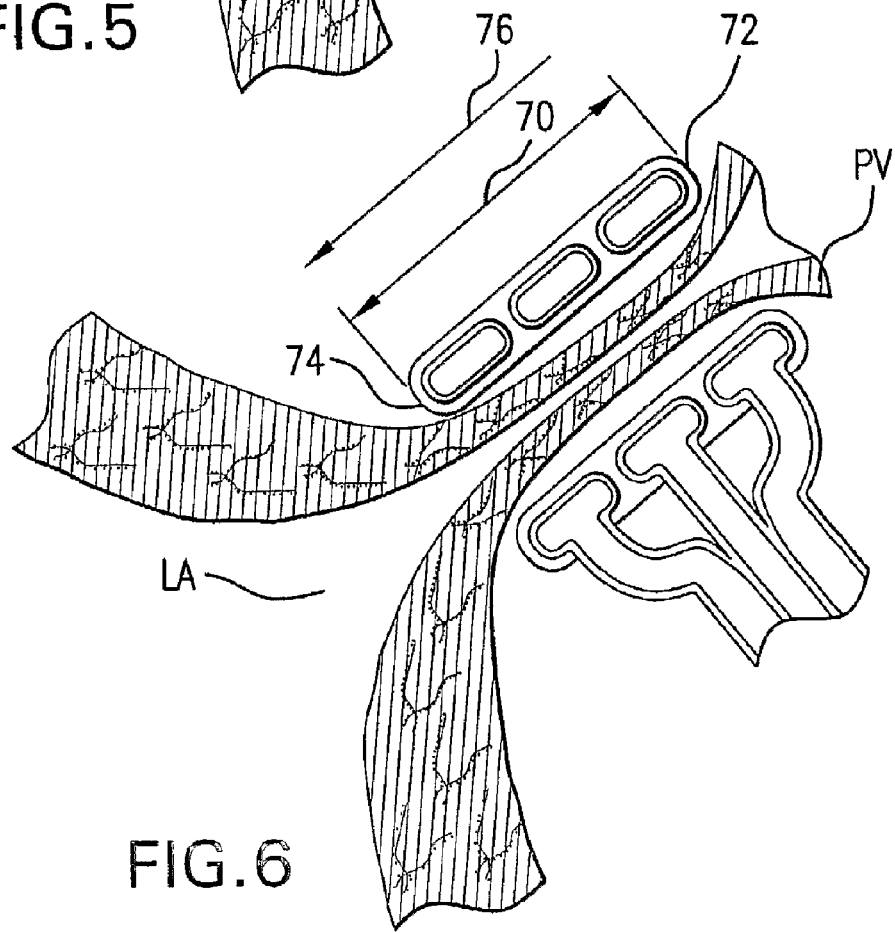
FIG. 6 is a sectional view of the prosthetic partitioning device in a second, more restricted flow configuration, in accordance with the present invention.

In order to partition the flow between the left atrium LA and the pulmonary vein PV (and the lungs), the prosthetic partitioning device is transitioned from a first configuration (illustrated in FIG. 5), which allows substantially unrestricted flow of fluid, e.g., blood, through the body conduit, to a second configuration inhibiting the flow of fluid, e.g., of blood, from the left atrium LA into the pulmonary vein PV. According to an exemplary embodiment, this transition may occur in a wave-like fashion from one end of the prosthetic partitioning device to the other end. As illustrated in FIG. 6, the transition may occur initially at the distal end 72 of the prosthetic partitioning device 12, and continue along the length 70 of the device to the proximal end 74 thereof, i.e., from the end farthest from the left atrium LA to the end closest to the left atrium LA. As the transition from a first configuration to a second configuration occurs towards the proximal end, the fluid within the conduit, e.g., blood within the segment of the PV, to which the prosthetic partitioning device 12 is coaxially attached, is propelled proximally, e.g., from pulmonary vein PV into the left atrium LA. (As indicated by arrow 76.) Conversely, when the prosthetic partitioning device 12 is transitioned from the second configuration, which allows no flow of fluid or a restricted flow of fluid through the pulmonary vein PV, to the first configuration which allows substantially unrestricted flow of fluid through the central passage 26, it is also transitioned from its distal end 72 (e.g., the end furthest from the left atrium) toward its proximal end 74, permitting and facilitating the flow of fluid, e.g., of blood, during the transition toward its proximal end, i.e., from the pulmonary vein PV into the left atrium LA. In the case of a failure of the device, the balloons 20 would return to the uncompressed state (illustrated in FIG. 5), thereby allowing unrestricted flow of blood through the pulmonary vein PV.

With continued reference to FIGS. 2 and 3, the control device 14 may be a generator, of a type substantially identical to that which is used with cardiac pacemakers. The control device 14 is typically a small, hermetically sealed programmable computer device, including a lithium or similar battery to supply power for the generator, which is housed in a container having typical dimensions of about half an inch deep and one and a half inches wide, and fabricated of a biocompatible material, such as titanium. As illustrated in FIG. 2, the control device 14 is typically implanted under the skin beneath the left clavicle (collarbone). The control device 14 discharges and effects the transition of each prosthetic partitioning device 12 between a less restricted flow configuration to a more restricted flow configuration. In the exemplary embodiment, an activator cable 18 to activate each prosthetic partitioning device 12 is connected to the control device 14, and is used to transmit a control signal from the control device 14 to the prosthetic partitioning device 12 to effectuate such transition. As illustrated in FIGS. 2 and 3, activator cable 18 may be connected to the pump 40, which in turn activates the prosthetic partitioning device. Alternatively, it is understood that the control device 14 may signal the transition of the prosthetic partitioning device 12 without the use of activator cables by the use of wireless technology known in the art, such as Bluetooth technology. The use of such wireless technology would permit at least a portion of the control device 14 to be located outside the patient.

The sensor device receives an input relating to characteristics or physiological parameters of the patient's body. In the exemplary embodiment, sensor device may include a pair of sensor leads 16a and 16b. As illustrated in FIG. 2, sensor lead 16a may be a standard pacemaker lead, which is placed in the right ventricle RV of the patients heart and, if the patient is not in atrial fibrillation, another sensor 16b, i.e., another pacemaker lead, is placed in the right atrium RA. According to another exemplary embodiment, a lead may alternatively be placed in the left ventricle LV via the cardiac vein. The sensor devices 16a and 16b typically detect electrical activity in the chambers of the heart in which they are implanted and transmit that information to the control device 14. In the exemplary embodiment, sensor device may include flexible insulated electrical wires 50a and 50b which are connected to the control device 14. According to another embodiment, it is understood that the sensor devices may transmit the information to the control device 14 without the use of connecting wires by the use of wireless technology known in the art, such as Bluetooth technology. As discussed above, at least a portion of the control device 14 may be located outside the patient. In another embodiment, the sensor devices may be pressure transducers which detect pressure in the chamber of the heart in which they are implanted and transmit information to the control device 14.

According to a further embodiment, the control device provides signals to the prosthetic partitioning device without the use of a sensor device. In such embodiment, the control device may signal the prosthetic partitioning device to provide the transition between the first configuration and the second configuration without detecting physiological parameters of the patient. Such signaling may be done according to a predetermined transition scheme, or may be modulated among a plurality of predetermined transition schemes.

The system 100 in accordance with the invention, when it includes prosthetic partitioning devices 12 located in and/or about all or several pulmonary veins PV, partitions fluid flow during selected time periods. More particularly, the prosthetic partitioning devices 12 provide relief of or eliminates congestive heart failure due to either or both of the two above-described etiologies, i.e., defective systolic partitioning and/or defective diastolic partitioning of flow into the pulmonary veins, both which create increased pulmonary venous pressure. For example, in patients with congestive heart failure with abnormally high mean pulmonary venous pressure due to defective systolic partitioning between the left ventricle and the pulmonary veins largely or partially secondary to mitral regurgitation, who are deemed unsuitable for mitral valve replacement, repair or modification, implantation of prosthetic partitioning devices 12 as described herein, results in lower mean pulmonary venous pressure by restoring effective systolic partitioning between relatively high left ventricular and left atrial systolic pressure, and pulmonary veins. Accordingly, the sensor devices, leads 16a and/or 16b may be used to detect the onset of electrical and/or mechanical systole of the left ventricle LV and transmit such information to the control device 14. The control device 14 would then transmit a signal to the one or more prosthetic partitioning devices 12 to effect a transition to the flow-restricted condition, in order to reduce pressure in the pulmonary vein PV. The timing of the signal for activation will depend on the site of the sensing and the time required for activation.

In patients with congestive heart failure largely or partially due to left ventricular diastolic dysfunction or mitral stenosis, with abnormally high mean pulmonary venous pressure due to natural lack of diastolic partitioning between the left atrium and pulmonary veins, or due to abnormal opening of the mitral valve MV, implantation of the prosthetic partitioning devices 12 results in lower mean pulmonary venous pressure by creating effective diastolic partitioning between relatively high left atrial diastolic pressure and the pulmonary veins. Accordingly, the sensor devices may be used to detect the onset of electrical and/or mechanical diastole of the left atrium LA and transmit such information to the control device 14. The control device 14 would then transmit a signal to the one or more prosthetic partitioning devices 12 to effect a transition to the more flow-restricted condition, in order to reduce pressure on the pulmonary vein PV.

Pressure transducers may be implanted in the left atrium LA and/or left ventricle LV in the same manner as leads 16a and 16b transceptally, as is known in the art. The prosthetic partitioning devices 12, in their properly implanted condition, configuration and orientation, are thus capable, by the timing and direction of their activation, of permitting and facilitating egress of blood from the pulmonary veins, into which they are implanted, into the left atrium only during that portion of the cardiac cycle when the pressure in the said pulmonary vein slightly exceeds, or is about to exceed the pressure in the left atrium, and are capable of preventing egress of blood from the left atrium into the said pulmonary veins during that portion of the cardiac cycle when the pressure in the left atrium exceeds the pressure in the said pulmonary vein.

Figure 7:
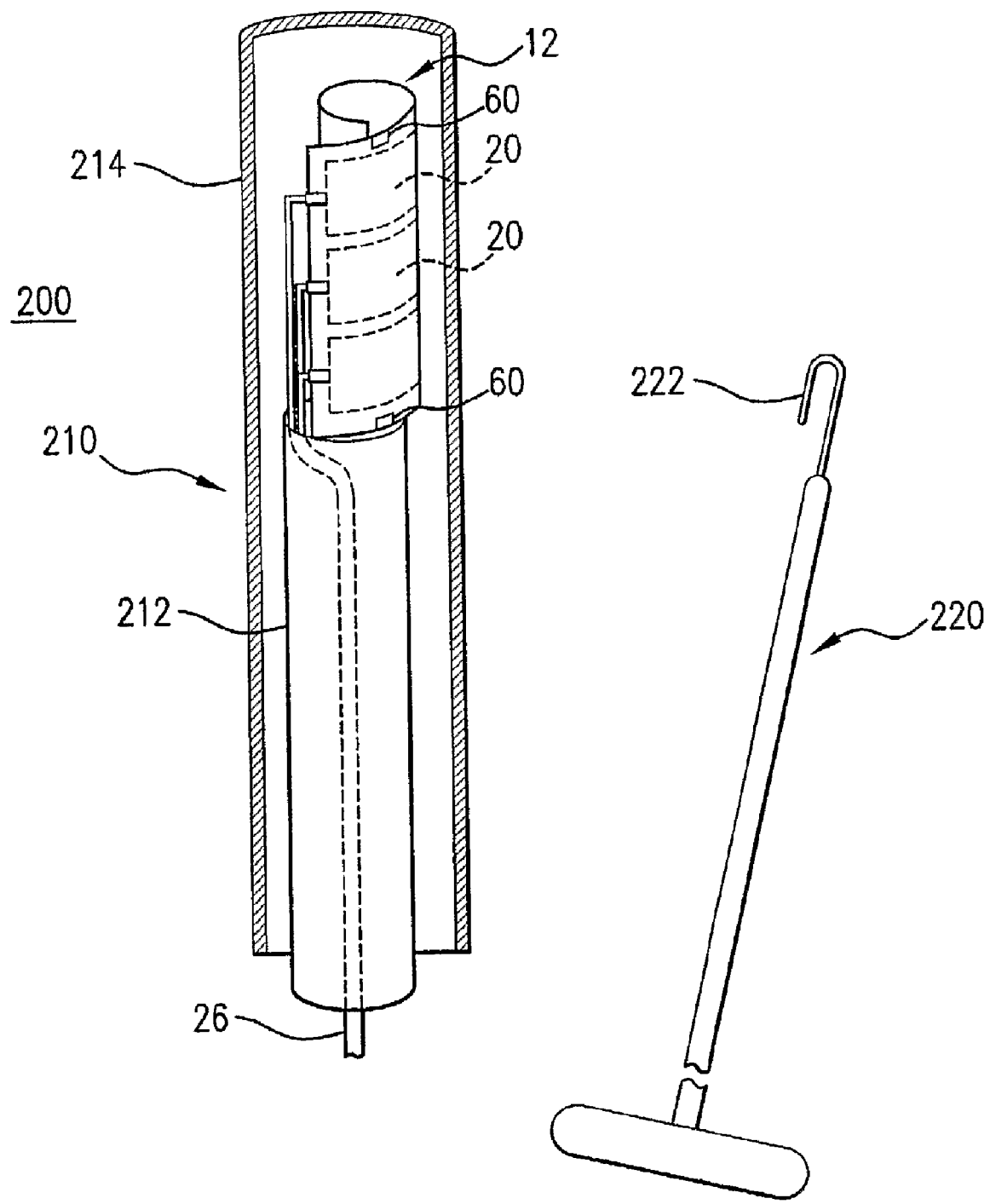
FIG. 7 is a view of a delivery system in accordance with the present invention.

The assembly of a delivery system 200 in accordance with the invention is described herein. An appropriately sized prosthetic partitioning device 12 is selected according to the diameter of the target body conduit (e.g., pulmonary vein PV) at the implantation site. The prosthetic partitioning device 12 is disposed on the prosthetic partitioning device-carrying segment 212 of a delivery catheter 210, preferably in a rolled or compressed configuration, as illustrated in FIG. 7. The prosthetic partitioning device 12 is securely attached on the expandable prosthetic partitioning device-carrying segment 212. The prosthetic partitioning device 12 may be attached to the device carrying segment 212 by passive compression, and may optionally include retention cuffs. The prosthetic partitioning device 12 is maintained in the desired location on the expandable prosthetic partitioning device-carrying segment 212 until expansion of the device 12 in the pulmonary vein PV by the operator. The prosthetic partitioning device 12 may be protected from damage or disruption during its passage to and within the body conduits of the patient by use of the sheath 214. Markers clearly visible or palpable during the procedure, e.g., radiopaque markers 60, are affixed to the prosthetic device 12 and/or the device-carrying segment 212 to identify the location of such prosthetic partitioning device 12 and the device-carrying segment 212 during such procedure. Furthermore, prosthetic partitioning device 12 and delivery system 200 of the invention may be coated with or incorporating biological, chemical, pharmacological or radioactive substances, coatings or adhesives, including but not limited to anticoagulant and antiproliferative substances. Also illustrated in FIG. 7 is a retractor 220 having an atraumatic tool element 222, to assist deployment of the prosthetic partitioning device, as will be described below. The assembly is sterilized, packaged, and labeled as is appropriate for its components and intended application(s).

Figure 8:
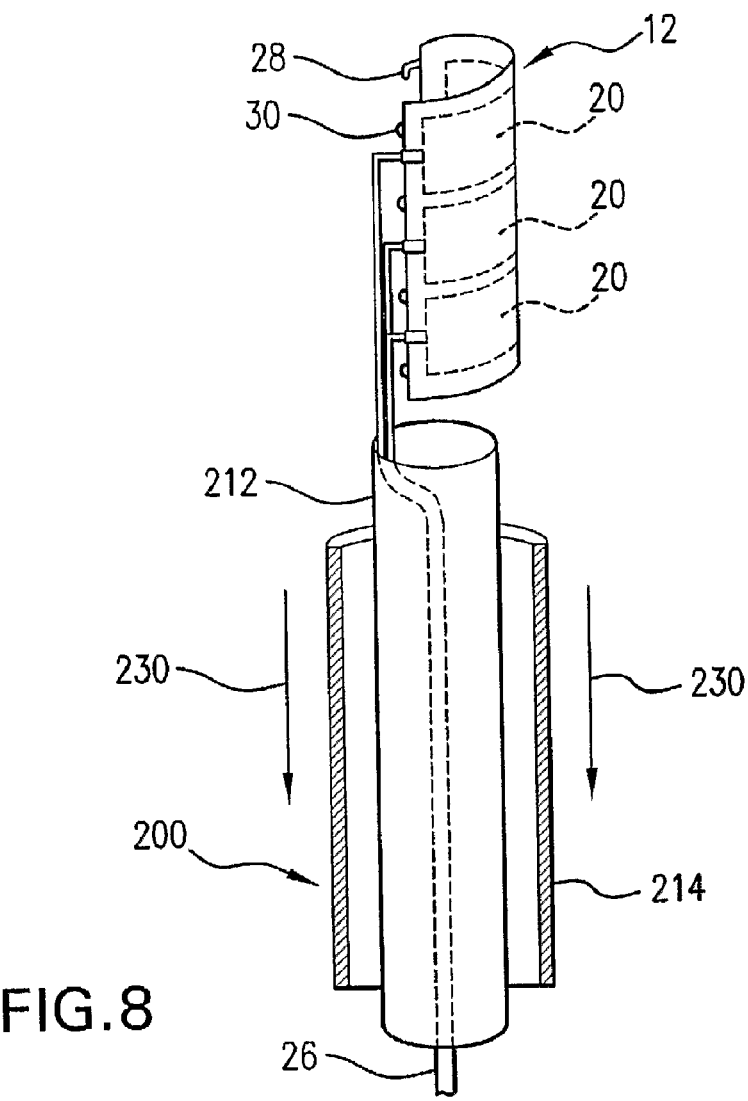
FIG. 8 is a view of the delivery system of FIG. 7 in a partially deployed configuration, in accordance with the present invention.
Figure 9:
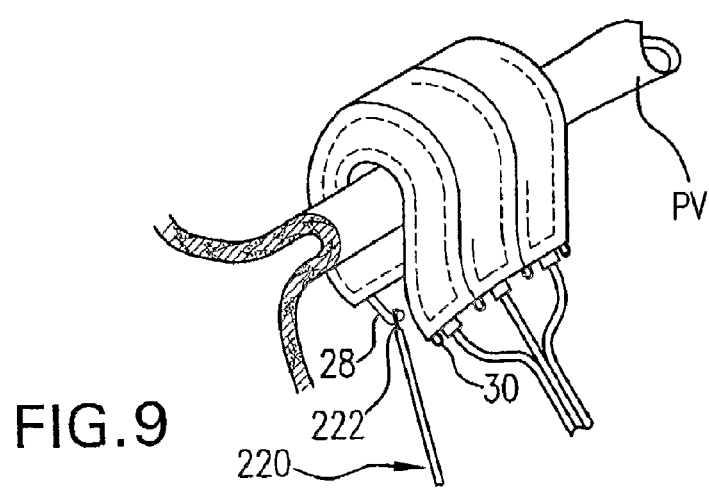
FIG. 9 is a view, in partial section, of the installation of the prosthetic partitioning device of FIGS. 3-6, in accordance with the present invention.

A technique for the surgical deployment of the prosthetic partitioning device 12 into and/or about a body conduit, e.g., target pulmonary vein PV, during an open-chest and/or laparoscopic/endoscopic/minimally invasive procedure is described herein, and illustrated in FIGS. 8-9. With the patient under appropriate anesthesia, access to a pulmonary vein PV as it enters the left atrium LA is attained using standard surgical techniques. The prosthetic partitioning device delivery system 200 of the invention, with such a prosthetic partitioning device 12 securely attached thereto, is inserted into or placed into the proximity of and substantially around the target pulmonary vein PV under direct visualization or through the use of laparoscopic cameras by the implanting surgeon. The distal end of the delivery system 200 is advanced into the desired location in and/or about the target pulmonary vein.

The prosthetic partitioning device 12 is then deployed as specified herein. According to one embodiment, the prosthetic partitioning device 12 is attached to the prosthetic partitioning device-carrying segment 212 and includes a self-expanding characteristic (as will be described herein), the protective sheath 214 is retracted in the direction indicated by arrows 230, as illustrated in FIG. 8. The prosthetic partitioning device 12 is thus exposed. The prosthetic partitioning device 12 is permitted to expand from the compressed condition illustrated in FIG. 7. For example, gas or fluid may be introduced into balloons 20 via the supply line 26, to cause slight expansion of the prosthetic partitioning device 12, and to cause its separation from the prosthetic partitioning device-carrying segment 212. Retractor 200 or similar device may be used to position the prosthetic partitioning device 12 about the pulmonary vein PV. The tool portion 222 may be used to secure the prosthetic partitioning device 12 in position. For example, the hook 28 and loop 30 configuration may be manipulated to secure the device 12 to the pulmonary vein PV (See FIG. 9). Alternatively, sutures, clips, stents, or other devices known in the art may be used. After the implantation of the prosthetic partitioning device 12, the said delivery system 200 is removed from the patient P. If it is desired to implant two or more prosthetic partitioning devices 12, the portion of the pulmonary vein PV to be treated is then identified, and the process is repeated, until the desired number of prosthetic devices are successfully implanted in all of the desired pulmonary veins.

Following the implantation of the prosthetic partitioning devices, the control device 14 may be implanted as described above (see FIG. 2). The activator cable 18 is then connected to control device 14, which, when activated, discharges and repetitively effects the transition of each prosthetic partitioning device 12 connected to it between the first, less restricted flow configuration to the second, more restricted flow configuration. For a surgical implantation over the target pulmonary vein PV, the activator cable 18 is tunneled by the surgeon to the pump, such as external pump 40. Sensor devices, such as leads 16a and 16b, are placed in the right ventricle RV and/or in the right atrium RA. Leads 16a and 16b are connected via cables 50a and 50b to the control device 14, which is programmed to effect partitioning during appropriate portions of the cardiac cycle when pressure in the left atrium may be higher than in pulmonary veins.

Where the prosthetic partitioning device 12 is placed outside, e.g., substantially around and over, the target pulmonary vein PV, the prosthetic partitioning device is a device which, when activated, is capable of compressing the target pulmonary vein at the site of implantation, impeding flow through its lumen. Additional exemplary prosthetic partitioning devices are described herein.

Figure 10:
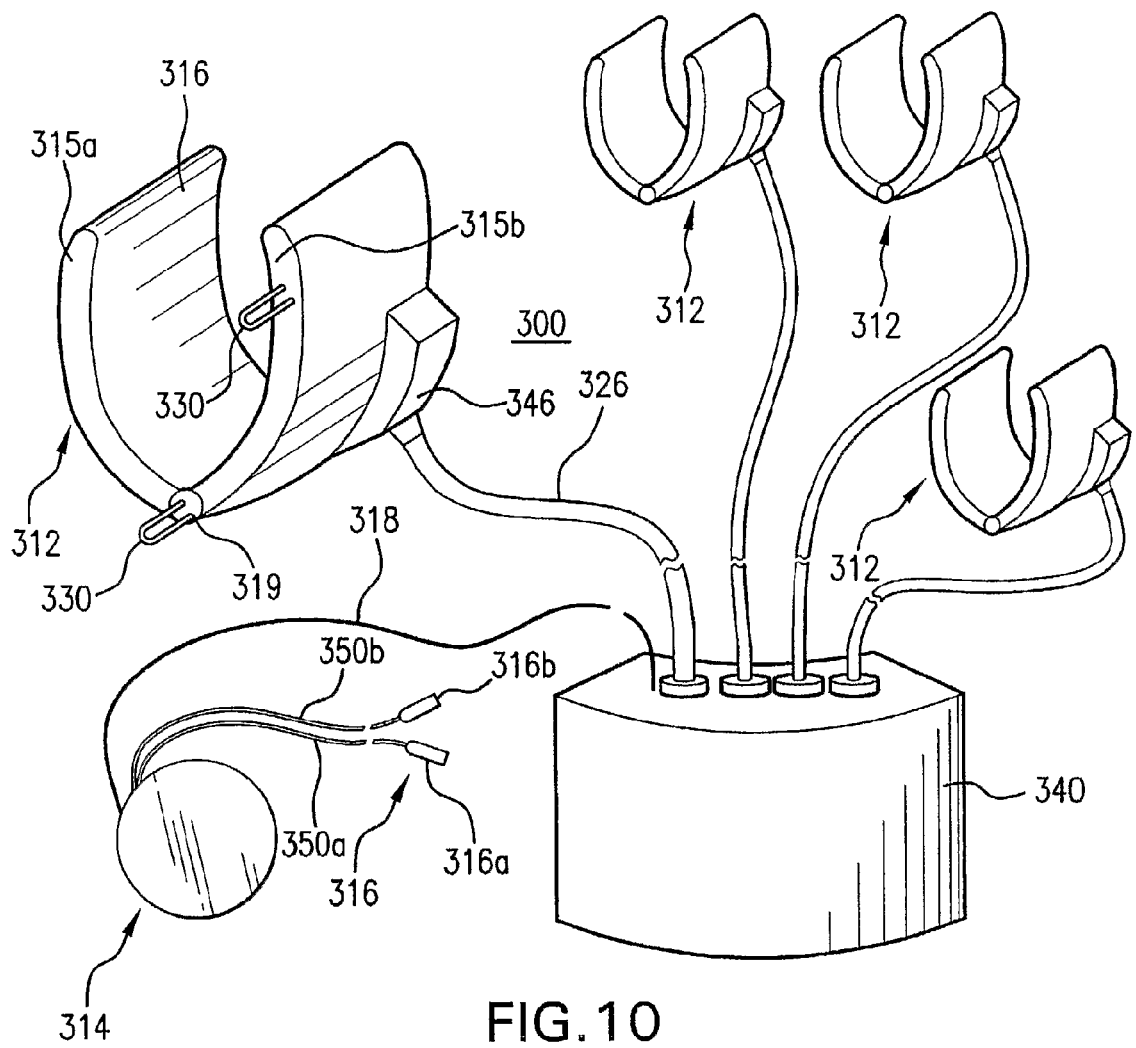
FIG. 10 is a view of another exemplary embodiment of the system, in accordance with the present invention.

Another alternative embodiment of the system for partitioning the body conduit of a patient is system 300, illustrated in FIG. 10 (not to scale). System 300 is substantially identical to the system described above, with the differences noted herein. System 300 includes a prosthetic partitioning device 312 positioned at the body conduit to be effectively partitioned, a control device 314 for actuating the prosthetic partitioning device 312, and a sensor device 316. In the exemplary embodiment, the prosthetic partitioning device 312 is positioned about the pulmonary vein PV to restrict flow therethrough.

In accordance with an exemplary embodiment, prosthetic partitioning device 312 includes a structure that permits coaxial attachment to the body conduit, e.g., the pulmonary vein PV. The prosthetic partitioning device 312 may be activated by the control device 314, as described herein. As will be further described herein, the prosthetic partitioning device 312, is repetitively transitioned between a first configuration, which allows less restricted or substantially unrestricted flow of fluid, e.g., blood, to a second configuration, which restricts the flow of fluid therethrough.

Figure 11:
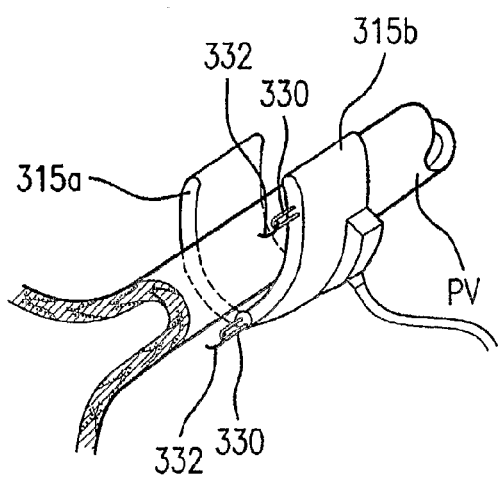
FIG. 11 is a view, in partial section, of the prosthetic partitioning device of FIG. 10 installed about a patient's body conduit, in accordance with the present invention.

System 300 includes a pair of clamping arms 315a and 315b, pivotable about a hinge portion 316 for engaging the exterior wall of the pulmonary vein PV with atraumatic interior surfaces 318. As illustrated in FIG. 11, the prosthetic partitioning device 312 may be positioned about the pulmonary vein PV or other body conduit and secured by the use of sutures 332 applied through loops 330 on the device 312, or alternatively by sutures, clips, or stents, as is known in the art. With continued reference to FIG. 3, prosthetic partitioning device is provided with a hydraulic piston 346, as is known in the art. Fluid (e.g., gas or liquid) is supplied to the hydraulic piston 346 via supply line(s) 326 is provided by a pump, such as external pump 340.

Figures 12, 13:
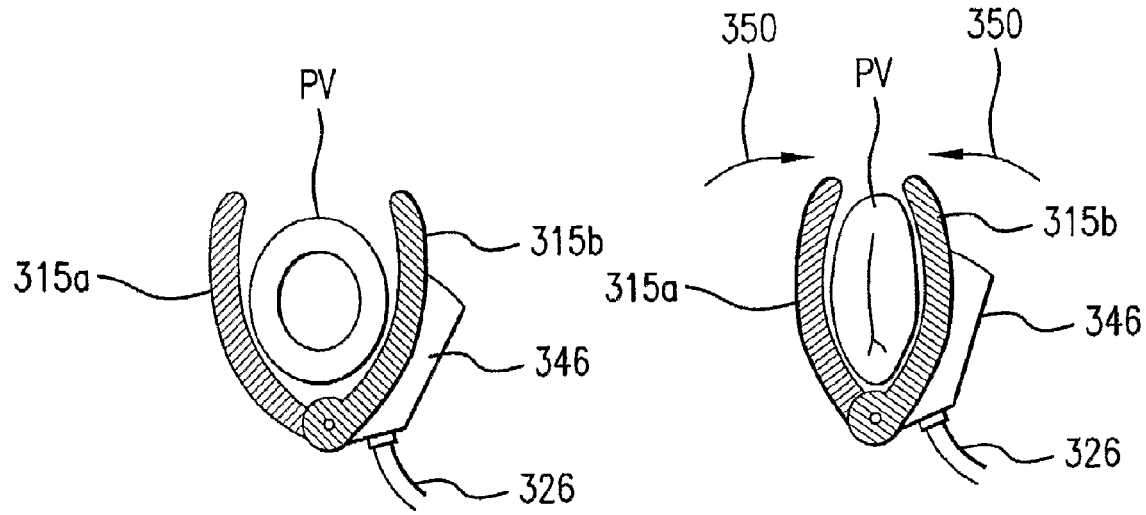
FIG. 12 is a cross-sectional view of the prosthetic partitioning device of FIG. 10 about a patient's body conduit in a first, less restricted flow, configuration, in accordance with the present invention.
FIG. 13 is a cross-sectional view of the prosthetic partitioning device of FIG. 10 about a patient's body conduit in a second, more restricted flow, configuration, in accordance with the present invention.
Figure 14:
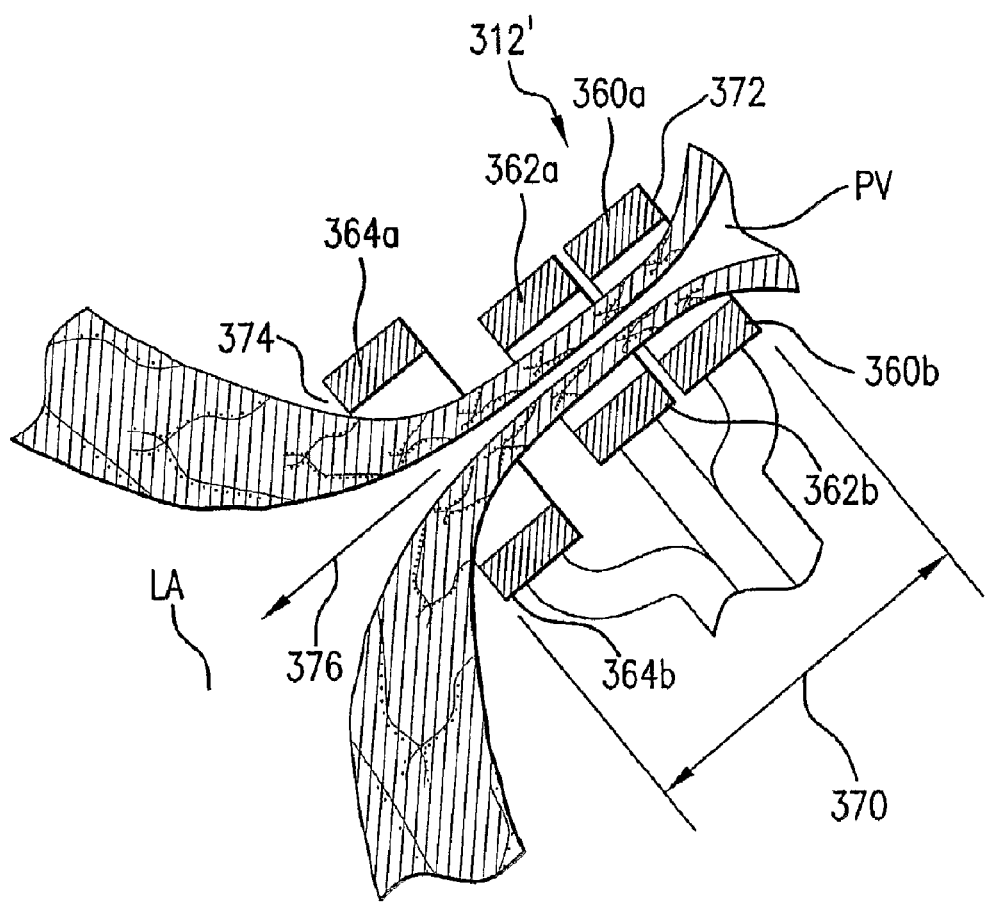
FIG. 14 is a longitudinal sectional view of another exemplary embodiment of the invention, installed about a patient's body conduit, in accordance with the present invention.

In order to partition the flow between the left atrium LA and the pulmonary vein PV (and the lungs), the prosthetic partitioning device 312 is transitioned from a first configuration (illustrated in FIG. 12), which allows substantially unrestricted flow of fluid, e.g., blood, through the body conduit, to a second configuration (illustrated in FIG. 13) inhibiting the flow of fluid, e.g., of blood, from the left atrium LA into the pulmonary vein PV. According to another exemplary embodiment, the transition may occur in a wave-like fashion from one end of the prosthetic partitioning device to the other end. As illustrated in FIG. 14, prosthetic partitioning device 312' is substantially identical to prosthetic partitioning device 312. However, prosthetic partitioning device 312' is provided with a plurality of pairs of clamping arms 360a/360b, 362a/362b, and 364a/364b. A transition from the first unrestricted flow configuration to the second more restricted flow configuration may occur initially at the distal end 372 of the prosthetic partitioning device 312', and continue along the length 370 of the device to the proximal end 374 thereof, i.e., from the end farthest from the left atrium LA to the end closest to the left atrium LA. In particular, the multiple pairs of clamping arms may be closed sequentially, i.e., clamping arms 360a/360b would be closed first, followed by clamping arms 362a/362b, and finally followed by clamping arms 364a/364b. As the transition from a first configuration to a second configuration occurs towards the proximal end, the fluid within the conduit, e.g., blood within the segment of the PV, to which the prosthetic partitioning device 312' is coaxially attached, is propelled proximally, e.g., from pulmonary vein PV into the left atrium LA. (As indicated by arrow 376.) Conversely, when the prosthetic partitioning device 312' is transitioned from the second configuration to the first configuration, it is also transitioned from its distal end 372 toward its proximal end 374, permitting and facilitating the flow of fluid, e.g., of blood, during the transition toward its proximal end, i.e., from left atrium LA into the pulmonary vein PV.

In the case of a failure of the device 312 or 312', a spring element (not shown) would be provided to return the clamping arms 315a/315b (or 360a/360b, 362a/362b, and 364a/364b) to the spaced apart configuration (illustrated in FIG. 12) allowing less restricted flow of blood through the pulmonary vein PV.

Figure 15:
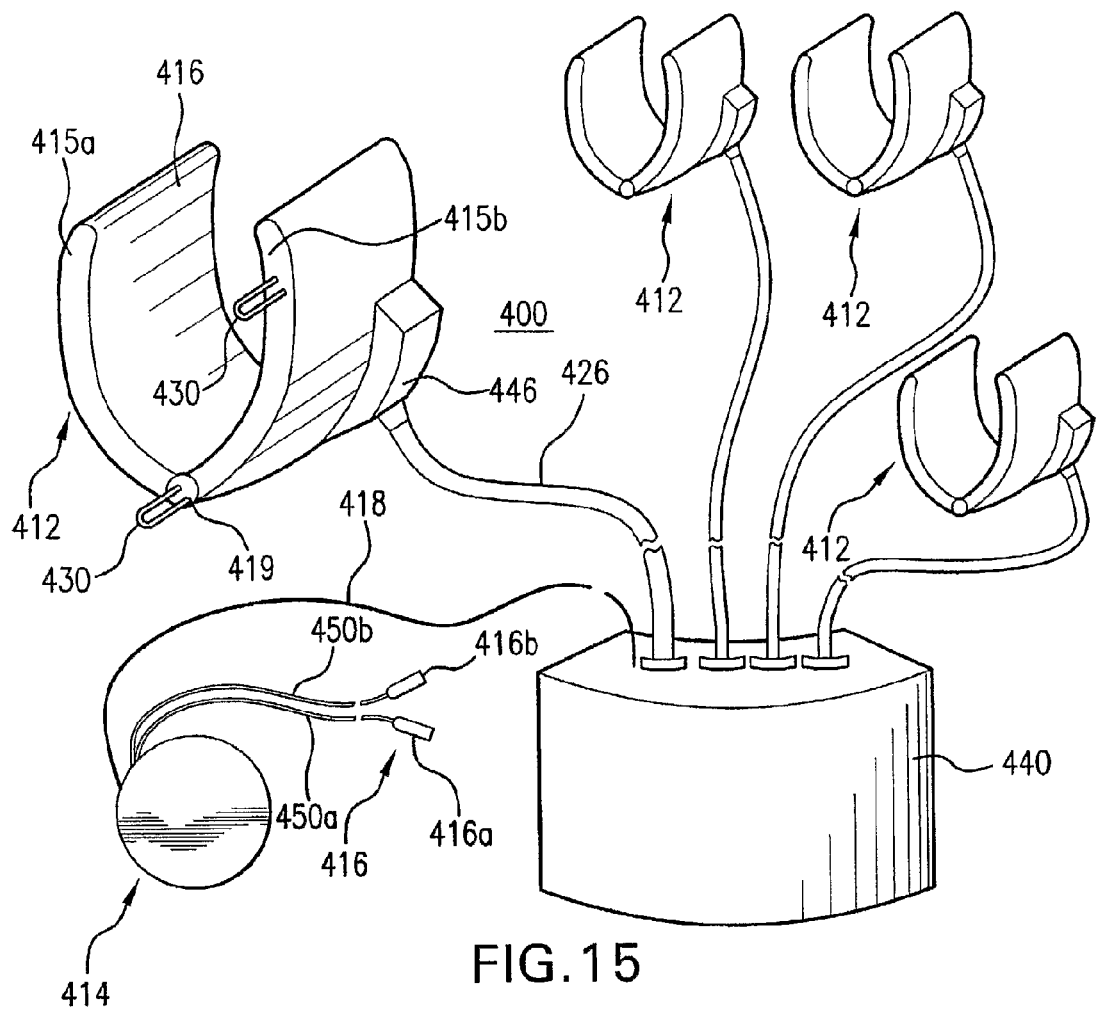
FIG. 15 is a view of another exemplary embodiment of the system, in accordance with the present invention.
Figure 16:
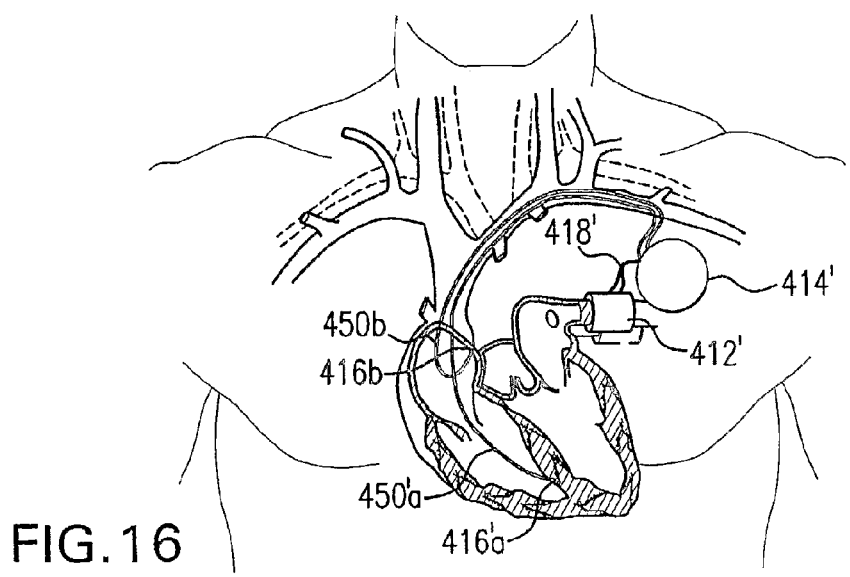
FIG. 16 is a simplified schematic view of a further exemplary embodiment of a system installed in a patient in accordance with the present invention.

Another alternative embodiment of the system for partitioning the body conduit of a patient is system 400, illustrated in FIG. 15 (not to scale). System 400 is substantially identical to the system described above, with the differences noted herein. System 400 includes a prosthetic partitioning device 412 positioned at the body conduit to be effectively partitioned, a control device 414 for actuating the prosthetic partitioning device 412, and a sensor device 416. In the exemplary embodiment, the prosthetic partitioning device 412 is positioned about the pulmonary vein PV to restrict flow therethrough.

In accordance with an exemplary embodiment, prosthetic partitioning device 412 includes a structure that permits coaxial attachment to the body conduit, e.g., the pulmonary vein PV. The prosthetic partitioning device 412 may be activated by the control device 414, as described herein. As will be further described herein, the prosthetic partitioning device 412, is transitioned from a first configuration, which allows substantially unrestricted flow of fluid, e.g., blood, to a second configuration, which restricts the flow of fluid therethrough.

System 400 includes a pair of clamping arms 415a and 415b, pivotable about a binge portion 416 for engaging the exterior wall of the pulmonary vein PV with atraumatic interior surfaces 418. As illustrated in FIG. 11 for the prosthetic partitioning device 312, prosthetic partitioning device 412 may be positioned about the pulmonary vein PV or other body conduit and secured by the use of sutures applied through loops on the device, or alternatively by sutures, clips, or stents, as is known in the art. With continued reference to FIG. 14, prosthetic partitioning device is provided with an electric motor 446, as is known in the art. Electrical power is supplied to the motor 446 via electrical line(s) 426 by a power supply, such as external battery 440.

In the case of a failure of the device 412, a spring element (not shown) would be provided to return the clamping arms 415a/415b to the spaced apart configuration (illustrated in FIG. 15) allowing unrestricted flow or less restricted of blood through the pulmonary vein PV.

According to another embodiment of the invention, system 400' is substantially identical to system 400, with the following differences noted herein. In particular, system 400' omits the external battery 440, such that power is supplied to the prosthetic partitioning device 412' by the power supply of control device 414'.

According to yet another embodiment of the invention, the electromechanical motor 446 of system 400 is substituted with an electromagnet (not shown) attached to one of the clamping arms, and which is selectively energized to attract the opposite clamping arm, thereby transitioning the prosthetic partitioning device from the first configuration to the second configuration. A spring element would be provided to return the clamping arms to the spaced apart configuration when the electromagnet is de-energized, thereby allowing unrestricted flow of blood through the pulmonary vein PV.

According to a still further embodiment (not shown), the prosthetic partitioning device is a transplant of skeletal muscle tissue (preferably autologous) onto the pulmonary vein. As discussed in U. Carraro et al., "Cardiac Bio-Assists: Biological Approaches to Support or Repair Cardiac Muscle, *Ital Heart J*, Vol 4, March 2003, 152-162, which is hereby incorporated by reference in its entirety herein, a portion of muscle tissue, such as the latissimus dorsi ("LD") muscle is wrapped around the body conduit to be partitioned. After healing, the LD muscle transplant is conditioned to fatigue resistance, and activated with a control device, such as control device 14, discussed above, to contract around the pulmonary vein PV, thereby partitioning the flow from the left atrium and the lungs. In contrast to the use of skeletal muscle for ventricular assist, the issue of potential fatigue of the LD or other skeletal muscle transplant is less critical, since the partitioning may occur only during selected periods (with no activity during other periods), thereby providing a rest period. (Moreover, a temporary decrease in transplant function has less clinical significance.) Following the implantation of the prosthetic partitioning devices, using either the percutaneous or surgical procedures, the activator cable 18 of each prosthetic partitioning device 12 is then connected to control device 14, which, when activated, discharges and effects the transition of each prosthetic partitioning device 12 connected to it from the less restricted flow configuration to the more restricted flow configuration. For the endoluminal percutaneous or surgical implantation, the activator cable 18, attached to the implanted partitioning device 12, is permitted to protrude freely out of the target pulmonary vein PV across the left atrium LA and the intra-atrial septum in the right atrium RA. Utilizing the entry site in the subelavian vein, required for the placement of the sensor devices 20a and 20b, a retrieval instrument is advanced into the right atrium RA, where it secures a portion of the activator cable and pulls it out through the superior vena cava and subclavian vein. Once the proximal end of the activator cable 18 is outside the patient's body, its length can be adjusted and the proximal end can be connected to the control device 14. For a surgical implantation over the target pulmonary vein PV, the activator cable 18, attached to the implanted partitioning device 12, is tunneled by the surgeon to the control device 14. Sensor devices 20a and 20b are placed in the right ventricle RV and/or in the right atrium RA. Sensor devices 20a and 20b are connected to the control device 14, which is programmed to effect partitioning during appropriate portions of the cardiac cycle when pressure in the left atrium may be higher than in pulmonary veins.

Figure 17:
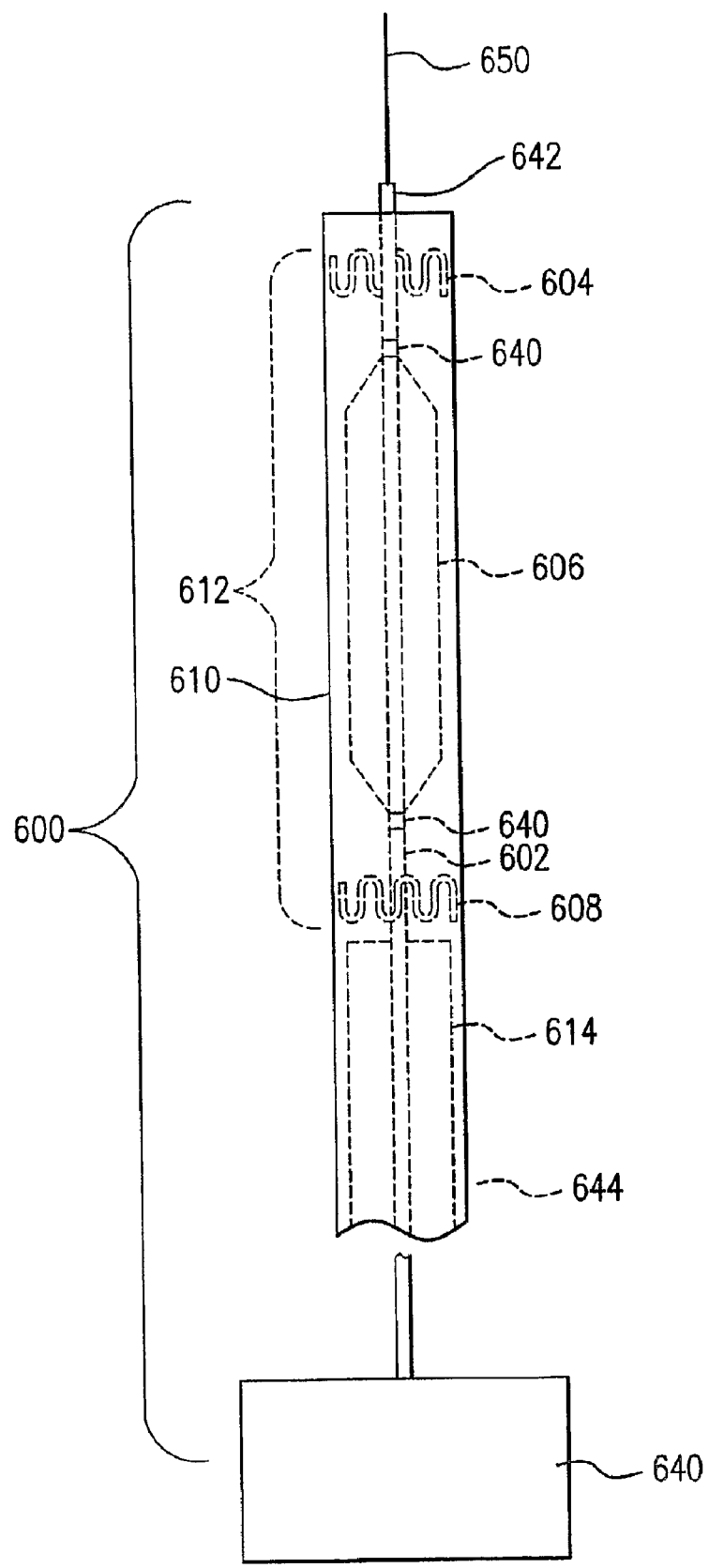
FIG. 17 is a longitudinal view of a still further exemplary embodiment of the prosthetic partitioning device and delivery apparatus, in accordance with the present invention.

Analogous devices may be used to deliver prosthetic partitioning devices via a percutaneous route. FIG. 17 illustrates an apparatus 600 for delivering such a prosthetic partitioning device 612 having a first end 642 which serves as the leading tip of the device as it is passed through the pulmonary vein and into the left atrium, and a second end 644. The prosthetic partitioning device 612 comprises a catheter 602 and, from first end 642 toward second end 644, a self-expanding anchoring stent 604, a balloon 606, and a self-expandable anchoring stent 608. The foregoing structures are enclosed, prior to placement, by a tubular retention sheath 610, which restrains the self-expanding stents 604 and 608 from expanding. A retaining tubular member 614 is used to position the prosthetic partitioning device within the lumen of the body conduit, such as the pulmonary vein PV. A pump, such as external pump 640, supplies gas or fluid to prosthetic partitioning device 612 to repetitively transition the device between the first less restricted flow configuration and the second, more restricted flow configuration.

Figure 18:
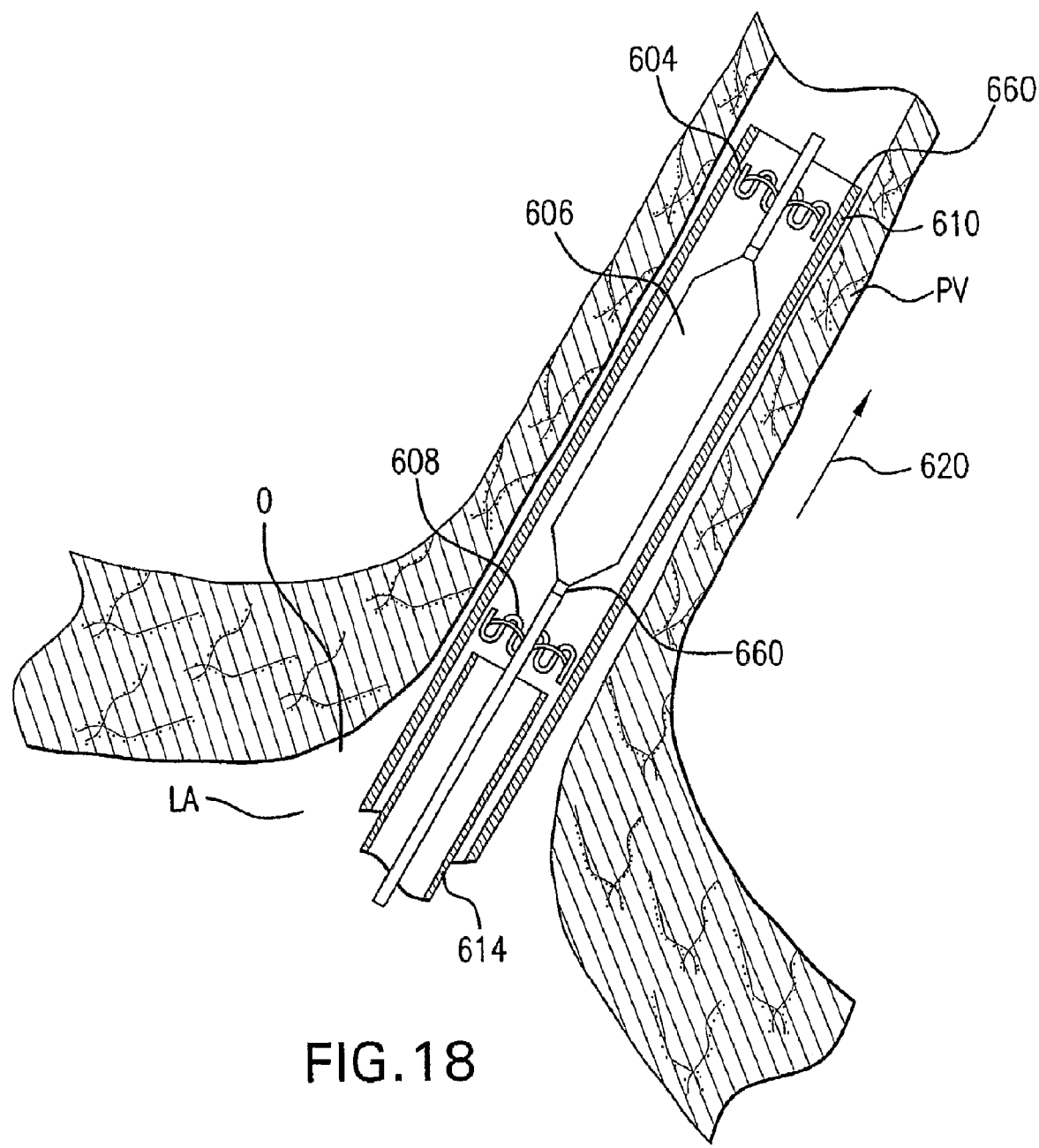
FIG. 18 is a longitudinal sectional view of an early stage of the installation of the embodiment of FIG. 17, in accordance with the present invention.
Figure 19:
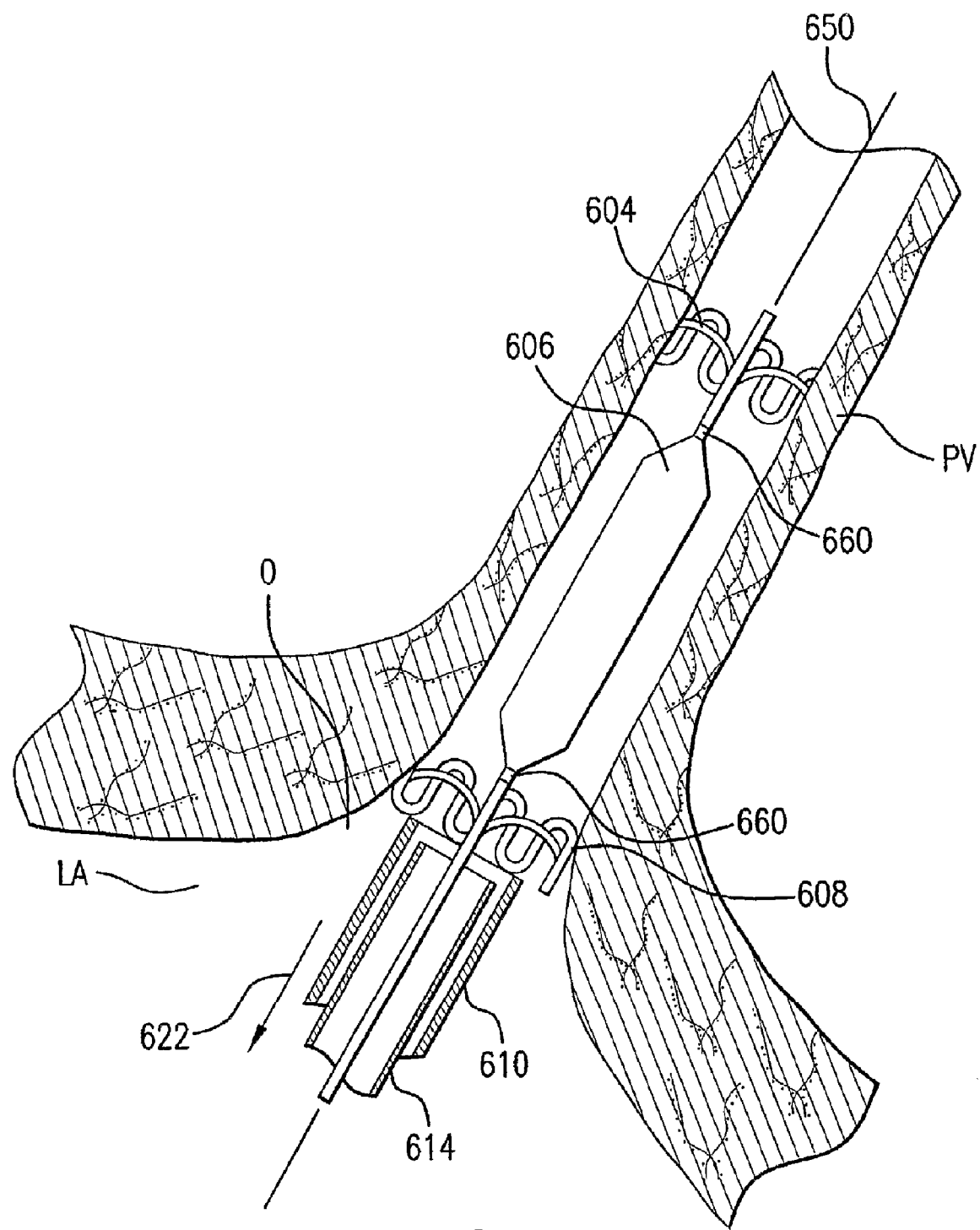
FIG. 19 is a longitudinal sectional view of a later stage of the installation of the embodiment of FIG. 17, in accordance with the present invention.
Figure 20:
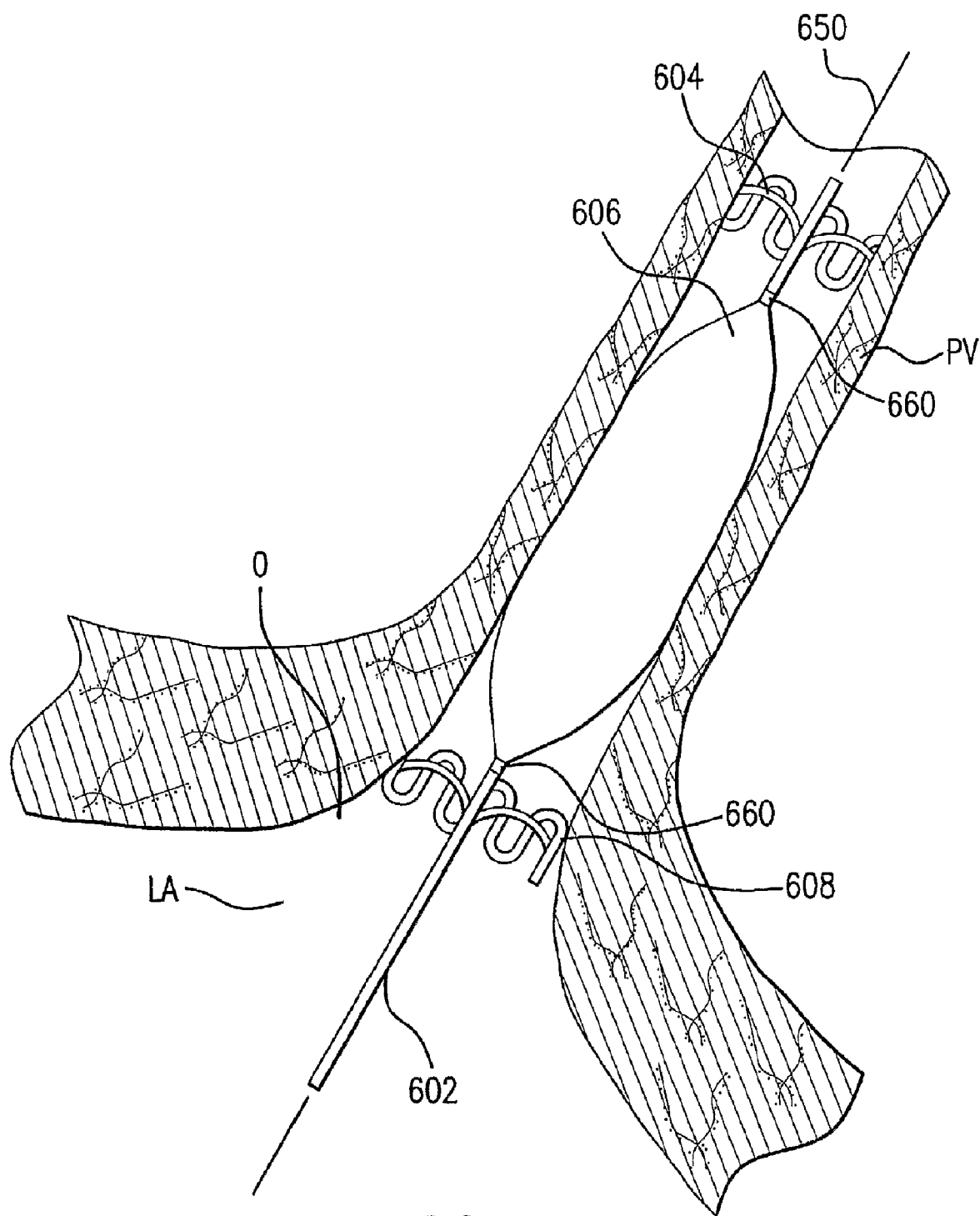
FIG. 20 is a longitudinal sectional view of the completed installation of the embodiment of FIG. 17, in accordance with the present invention.

FIGS. 18-20 depict, using cut-away views, a method of using the apparatus 600 shown in FIG. 17. FIG. 18 depicts a portion of a pulmonary vein PV. Also shown in FIG. 18 are the ostium O of the pulmonary vein PV and the left atrium LA. An arrow 620 shows the direction in which the device 600 is being inserted into the pulmonary vein PV. The device may be advanced such that the first end 640 lies within the pulmonary vein PV, as shown in FIG. 18. Then, as depicted in FIG. 19, the retention sheath 610 may be pulled back (in the direction of the arrow 622) while maintaining the retaining tubular member 614 in position, allowing self-expanding stents 604 and 608 to expand and engage the inner wall of the pulmonary vein PV, securing the prosthetic partitioning device 612 in position. Subsequently, the retention sheath 610 and the retaining tubular member 614 may be pulled back and withdrawn from the patient P.

In order to partition the flow between the left atrium LA and the pulmonary vein PV (and the lungs), the prosthetic partitioning device is transitioned from a first configuration (illustrated in FIG. 19), which allows substantially unrestricted flow of fluid, e.g., blood, through the body conduit, to a second configuration (illustrated in FIG. 20) inhibiting the flow of fluid, e.g., of blood, from the left atrium LA into the pulmonary vein PV. According to an exemplary embodiment, the first, substantially unrestricted flow configuration is achieved when the balloon 606 is in the unexpanded state, as shown in FIG. 19. The second, restricted flow configuration is achieved when the balloon 606 is expanded, e.g., by supplying helium, carbon dioxide, or saline to fill the balloon 606, as illustrated in FIG. 20. It is understood that the first flow configuration may alternatively be an assisted flow configuration, in which the balloon is expanded to increase the internal diameter of the body conduit, and therefore increase flow therethrough. For example, the balloon may have a non-circular shape, e.g., elliptical, such that when the balloon is expanded the walls of the pulmonary vein may be expanded to allow greater flow, but the elliptical shape of the balloon does not entirely block the interior lumen of the pulmonary vein. Alternatively, assisted flow in the first configuration may be achieved by inflating the balloon and deflating the balloon more rapidly than the body conduit wall is able to conform to the balloon. In such case, the wall of the body conduit remains expanded for a period of time after the balloon has contracted, thereby allowing less restricted flow therethrough.

According to another embodiment, attachment of the prosthetic partitioning device 612 to the interior of the body conduit is accomplished by an anchoring element, or anchoring stent having a non-self-expanding configuration (e.g., capable of plastic deformation) and is fabricated from steel, nitinol, titanium alloys, etc. The prosthetic partitioning device and the anchoring stent according to this embodiment may be deployed in a unexpanded configuration, and subsequently expanded in place by a balloon catheter or similar expansion device. Alternatively, for nitinol systems, expansion may occur upon reaching a desired temperature and/or electrical current. Depending on the size of the target pulmonary vein, such diameter may typically be greater than 10 mm and smaller than 25 mm. The length of the implantable prosthetic partitioning device 60 may typically be between 3 mm and 25 mm.

Radiopaque and/or palpable markers 660 may be provided on the prosthetic partitioning device 612 to identify the location of the prosthetic partitioning device 12 on the prosthetic partitioning device-carrying segment 212 of the delivery catheter 210 and after implantation. The marker may be radiopaque and located on the proximal and distal ends of the prosthetic partitioning device 12, as well as anywhere along it structure and elements. Furthermore, prosthetic partitioning device 12 and delivery system 200 of the invention are capable of being coated with or incorporating biological, chemical, pharmacological or radioactive substances, coatings or adhesives, including but not limited to anticoagulant and antiproliferative substances.

An exemplary technique for percutaneous deployment of the prosthetic partitioning device 612 into the body conduit of the patient, e.g., a target pulmonary vein PV, is described herein. An early step in this procedure is to access the right atrium RA percutaneously with an appropriate size guiding catheter which is advanced into the right atrium via a systemic vein, e.g. femoral vein, if necessary, the guiding catheter is advanced over a guide wire 650 and an introducer. A subsequent step is to access the left atrium by the same guiding catheter from the right atrium over a guide wire 650 and an introducer, by means of transceptal puncture. The guide wire 650 may be advanced through and out of the lumen of the delivery catheter 610 now positioned in the left atrium LA into the target pulmonary vein PV, under fluoroscopic guidance, and if necessary with localizing injections of radiographic dye. The preferred site of implantation of a prosthetic partitioning device 12 at the target pulmonary vein PV is then established and the diameter of the target pulmonary vein PV at the preferred site of implantation determined. Localizing injections of radiographic dye or intravascular ultrasound may also be used, if appropriate.

The prosthetic partitioning device delivery system 600 of the invention, having an appropriately-sized prosthetic partitioning device 612 (including the activator cable therewith) securely attached thereto, is coaxially mounted on the guide wire 650 by passing a guide wire through a guide wire lumen of the delivery system 600. The delivery system 600 of the invention is advanced coaxially over the guide wire 650, while maintaining the distal portion of the guide wire 650 in the target pulmonary vein, through and out of the lumen of the guiding catheter into the target pulmonary vein in the standard fashion, with the proximal end of the said delivery system remaining outside the patient at all times. The distal end of the delivery system 600, having the prosthetic partitioning device 612 attached thereto, is advanced to the desired location for deployment of the prosthetic partitioning device 612 in the target pulmonary vein PV over the guide wire 650. Once positioned in the desired location, the protective sheath 610 is withdrawn, thereby exposing the prosthetic partitioning device-carrying segment 614 of the said delivery system 600. For the embodiment in which the prosthetic partitioning device 612 is attached to self-expanding anchoring stents 604 and 608, the retraction of the protective sheath 610 from over the anchoring stents 604 and 608 permits the release and expansion of the prosthetic partitioning device-carrying segment 614, and the consequent expansion of the prosthetic partitioning device 612 and its anchoring stent 604 and 608 within the target pulmonary vein.

After the implantation of the prosthetic partitioning device 612, the said delivery system 600 is removed from of the patient. If implantation of more than one prosthetic partitioning device 612 is required, the guide wire is then repositioned in the second pulmonary vein, and the process is repeated, until all prosthetic devices are successfully implanted in all of the desired pulmonary veins.

Figure 21:
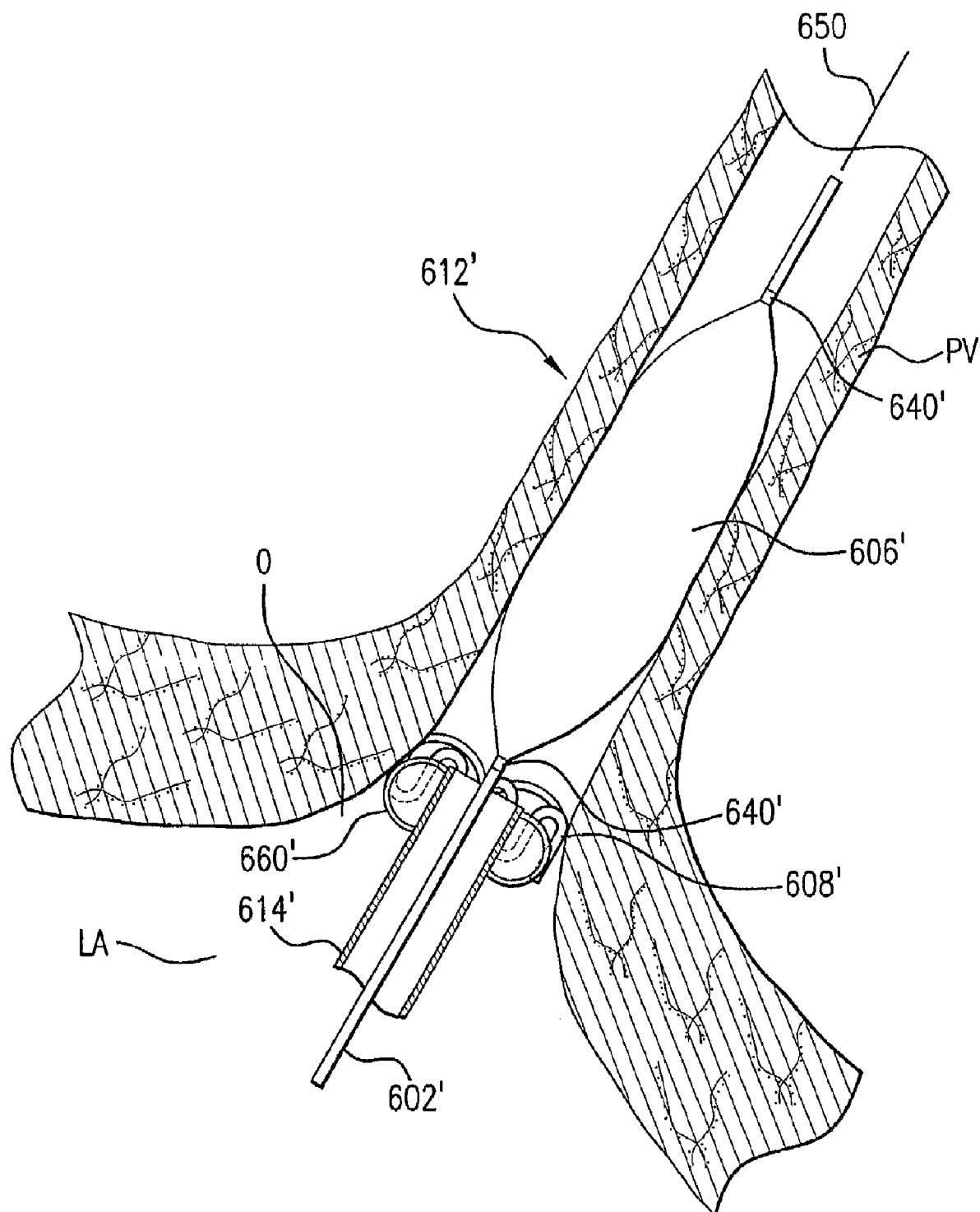
FIG. 21 is a longitudinal sectional view of the installation of another exemplary embodiment of the prosthetic partitioning device, in accordance with the present invention.

For the embodiment in which the prosthetic partitioning device 612' is attached to the prosthetic partitioning device-carrying segment 614 comprising a non-self-expanding anchoring stent 608' mounted on an appropriately sized balloon portion 660', the retraction of the protective sheath permits the expansion of the prosthetic partitioning device 612' and of the non-self-expanding anchoring stent 608' in the desired location in the target pulmonary vein by inflating the balloon portion 660' of the delivery system 600 to the appropriate pressure (FIG. 21). After the implantation of the prosthetic partitioning device 612', the balloon portion 660' may be deflated, and the said delivery system 600 is removed from the patient. The guide wire 650 may then be repositioned in the second pulmonary vein PV, and the process is repeated, until the desired prosthetic devices are successfully implanted in all of the desired pulmonary veins.

Figure 22:
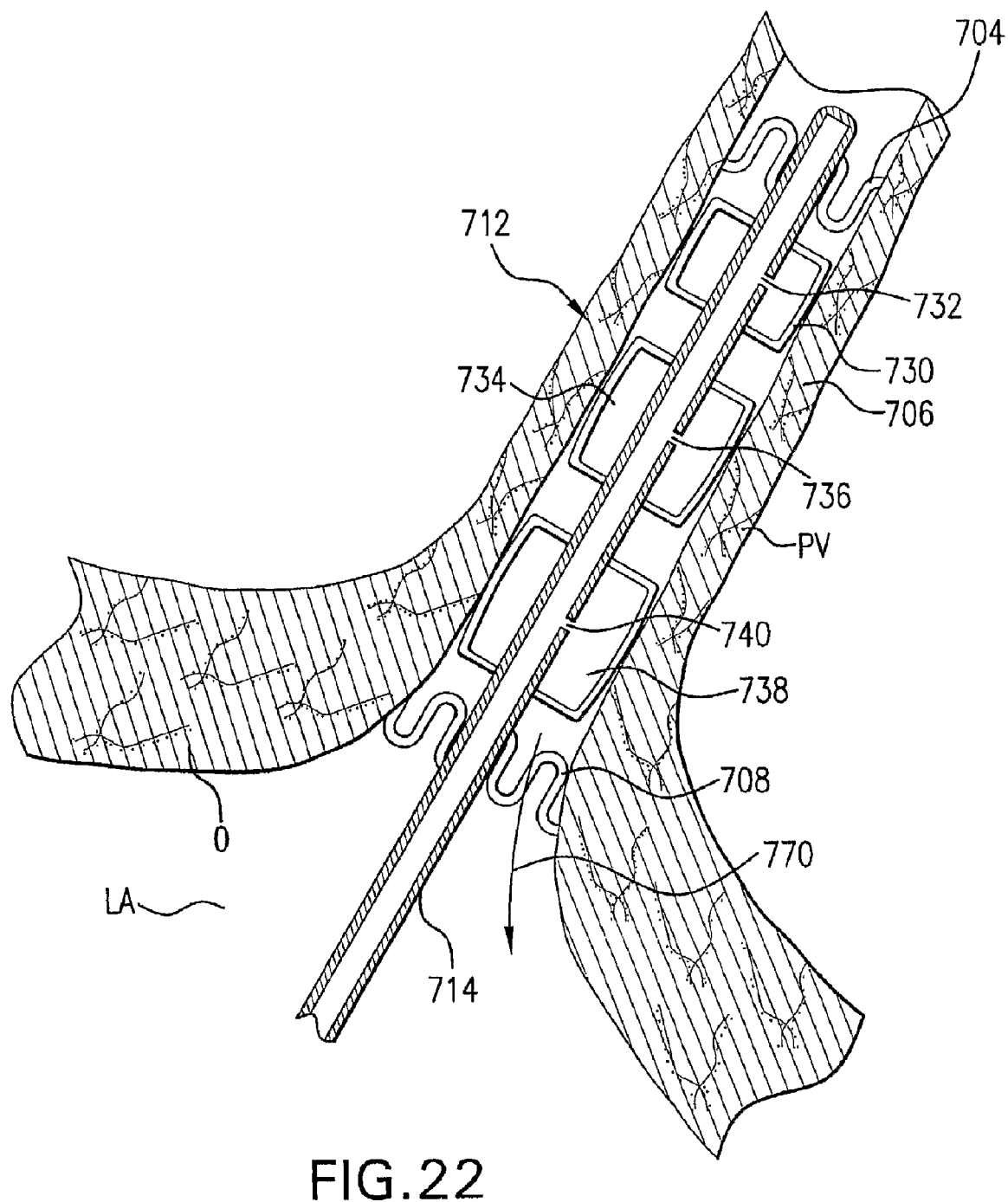
FIG. 22 is a longitudinal sectional view of the completed installation of yet another exemplary embodiment of the system, in accordance with the present invention.

In another exemplary embodiment, the transition from the first configuration to the second configuration is achieved in a wave-like fashion from one end of the prosthetic partitioning device to the other end. An intra-aortic balloon having a similar wave-like expansion is disclosed in U.S. Pat. No. 6,468,200, which is incorporated by reference herein. As illustrated in FIG. 22, a prosthetic partitioning device 712 is provided having a catheter 714 which provides for passage of an expansion fluid, e.g., helium, carbon dioxide, etc., for inflation and deflation of a segmented balloon 706 that is situated on a distal portion of the catheter 714. The balloon 706 has a first, distal chamber 730. An aperture 732 to the catheter 714 allows the expansion fluid to pass into and out of the chamber 730. A second chamber 734 adjacent the first chamber 730 has a larger volume than the chamber 730, and has an aperture 736 to the catheter 714. The aperture 736 may be smaller than the aperture 732. A third chamber 738 is situated proximal of the second chamber 734, i.e., closer to the left atrium LA, and is of greater volume than the chamber 734. The third chamber 738 has an aperture 740 to the catheter 714 that is smaller than the aperture 736. In this embodiment, the skin of the balloon 20 is a polyurethane film, which is selected for being flexible, but relatively inextensible. The prosthetic partitioning device 712 is anchored within the pulmonary vein PV as described above for prosthetic partitioning device 612, e.g., with the use of self-expanding stents 704 and 708 which are connected to the catheter 714 by used of self expanding spokes of the same material as the stents.

The prosthetic partitioning device 712 is inserted percutaneously via a lower limb artery into the right atrium RA, and then conveyed transceptally to the left atrium LA, in substantially the same manner as discussed above for prosthetic partitioning device 612 in FIGS. 17-20. A conventional balloon pump drive external to the patient is attached to the proximal end of the catheter 714 to force expansion gas into the balloon 706 and withdraw expansion fluid from it. Sensors substantially identical to sensors 16a/16b described above obtain the patient's heart cycle to control the transition of the prosthetic partitioning device 712 from the first configuration having substantially unrestricted flow to the second configuration having restricted flow.

The pumping cycle of the segmented balloon 706 is described herein. Because of the size differences in the chambers and in the respective apertures, the chamber 730 inflates first. The chambers inflate in sequence, with the chamber 734 inflating next, followed by inflation of the chamber 738. As the transition from a first configuration to a second configuration occurs towards the proximal end, the fluid within the conduit, e.g., blood within the segment of the PV, to which the prosthetic partitioning device 712 is coaxially attached, is propelled proximally, e.g., from pulmonary vein PV into the left atrium LA. (As indicated by arrow 770.) In the case of a failure of the device 712, the balloon 706 would return to the uninflated state, allowing unrestricted flow of blood through the pulmonary vein PV.

Remote monitoring of flow and pressure across the implanted prosthetic partitioning device, and blood temperature and oxygen saturation may be achieved by monitoring pressure transducers which may be implanted in the left atrium LA and left ventricle LV.

The prosthetic partitioning devices, such as prosthetic partitioning devices 12, 312, 412, 412', 612, 612', and 712 described herein, may be specified to serve a temporary function in a patient. For example, surgically implanted prosthetic partitioning devices may be used to stabilize temporarily a patient for whom mitral valve replacement may be eventually performed at some point in the future. The prosthetic partitioning device may also be used to provide an intermittent partitioning function. For example, a patient with congestive heart failure may be provided with intermittent partitioning. In such case, the prosthetic partitioning device may function only at night when an external power source is used. In order to minimize power source requirements, some patients may be provided with partitioning in all or only selected pulmonary veins PV during every cycle, during certain cardiac cycles, or only during exercise or when specific heart rate or hemodynamic criteria are met. Such intermittent or sequential partitioning may minimize structural and functional changes to the left atrium LA. In addition, the prosthetic partitioning device may be specified to operate only when the patient's heart rate is at or below a certain rate.

As discussed above, the prosthetic partitioning device is configured to remain in the first configuration, i.e., to allow unrestricted flow or less restricted of blood therethrough, in the absence of a control signal to transition to the second, restricted-flow configuration. Thus, the failure mode of the prosthetic partitioning device would be to remain in the first, inactivated configuration, e.g., due to depletion or malfunction of the power source. Thus, a failure of the system would result in a reversion to the patient's un-assisted function in the absence of the system. As discussed above, the balloon structures, such as prosthetic partitioning devices 12, 612, 612' and 712 would be in an uninflated state in the case of failure, thereby allowed un-assisted flow through the conduit. A spring element may be provided in prosthetic partitioning devices 312, 412, and 412' in order to maintain the clamping jaws in an open position, also allowing unrestricted flow through the conduit.

A procedure for treatment of target pulmonary vein obstruction due to a malfunction of certain types of prosthetic partitioning devices is described herein. For example, a prosthetic partitioning device implanted into a pulmonary vein may cause partial or complete obstruction of the target pulmonary vein due to complete or partial failure to resume a substantially unrestricted flow configuration, which may also result in the formation of thrombus in the prosthetic partitioning device. The method for treatment of such partial or complete obstruction of the target pulmonary vein by such a malfunctioning prosthetic partitioning device may include accessing the right atrium RA percutaneously with an appropriate size guiding catheter advanced into the right atrium RA, if necessary over a guide wire and an introducer, via a systemic, e.g. femoral, vein. Access to the left atrium LA is attained by the same guiding catheter from the right atrium over a guide wire and an introducer, by means of transceptal puncture. The guide wire is advanced through and out of the lumen of the catheter positioned in the left atrium LA, into the segment of the target pulmonary vein PV between the left atrium LA and prosthetic partitioning device. According to an exemplary embodiment, the advancement of the guide wire may be performed under fluoroscopic guidance, if necessary, with localizing injections of radiographic dye. The guide wire is then manipulated past the malfunctioning prosthetic partitioning device. If necessary, localizing injections of radiographic dye are used. A new delivery system having a new prosthetic partitioning device (including an anchoring stent if appropriate) is advanced coaxially over the guide wire, while maintaining the distal portion of the guide wire in the target pulmonary vein. The delivery catheter and the prosthetic partitioning device are advanced through and out of the lumen of the said guiding catheter into the target pulmonary vein in the standard fashion, such that the proximal end of the said delivery system is maintained outside the patient at all times. The distal end of the delivery system, comprising the prosthetic partitioning device (and the anchoring stent if appropriate), is advanced into the desired location overlapping the previously implanted prosthetic partitioning device in the target pulmonary vein over the said guide wire. The new prosthetic partitioning device or appropriate stent is deployed as described above, thereby compressing the malfunctioning first prosthetic partitioning device against the wall of the target pulmonary vein, and restoring partitioning of flow between the target pulmonary vein and the left atrium.

Provided the detailed disclosure herein, those skilled in the art may envision how the present invention could be practiced using alternative embodiments and variations thereof. The foregoing detailed description should be regarded as illustrative rather than limiting.

What is claimed is:

1. A system for reducing the mean pulmonary venous pressure in a pulmonary vein of a patient comprising:
   (a) a prosthetic partitioning device configured for coaxial attachment on the exterior of the pulmonary vein and movable between a first configuration permitting a less restricted blood flow through the vein and a second configuration permitting a more restricted blood flow through the vein, the transition between the first and second configuration of the device progressing along the length of the coaxially attached pulmonary vein; and
   (b) a control device configured to transmit signals to the prosthetic partitioning device to effectuate the transition from the first configuration to the second configuration, whereby assumption of the second configuration restricts blood flow and results in a lowering of mean pulmonary venous pressure.

2. The system according to claim 1, wherein the prosthetic partitioning device comprises an expandable component.

3. The system according to claim 2, wherein the control device configured to transmit signals to the prosthetic partitioning device comprises a control device configured to transmit a signal regarding flow of an expansion medium to the expandable component.

4. The system according to claim 1, wherein the prosthetic partitioning device is pneumatically actuated to move between the first configuration and the second configuration.

5. The system according to claim 1, wherein the prosthetic partitioning device is hydraulically actuated to move between the first configuration and the second configuration.

6. The system according to claim 5, wherein the control device configured to transmit signals to the prosthetic partitioning device comprises a control device configured to transmit a signal regarding flow of a hydraulic medium to the prosthetic partitioning device.

7. The system according to claim 1, wherein the prosthetic partitioning device is electromechanically actuated to move between the first configuration and the second configuration.

8. The system according to claim 1, wherein a plurality of the prosthetic partitioning devices are configured to be installed on a pulmonary vein.

9. The system according to claim 1, wherein the control device is configured to effectuate the transition from the first configuration to the second configuration during a predetermined time period.

10. The system according to claim 1, wherein the control device is configured to effectuate the transition from the first configuration to the second configuration at night.

11. The system according to claim 1, wherein the control device is configured to effectuate the transition from the first configuration to the second configuration during particular cardiac cycles.

12. The system according to claim 1, wherein the control device is configured to effectuate the transition from the first configuration to the second configuration when predetermined heart rate criteria are met.

13. The system according to claim 1, wherein the control device is configured to effectuate the transition from the first configuration to the second configuration when predetermined hemodynamic criteria are met.

14. The system according to claim 1, wherein the prosthetic partitioning device is configured to remain in the first configuration in the event of a malfunction of the system.

15. The system according to claim 14, wherein the prosthetic partitioning device is configured to remain in an uninflated configuration in the event of a malfunction of the system.

16. The system as claimed in claim 1, further comprising a sensor device for monitoring characteristics of the patient.

17. The system as claimed in claim 16, wherein the control devices is configured to receive signals from the sensor device and to transmit signals to the prosthetic partitioning device to effectuate the transition from the first configuration to the second configuration based on the signals received from the sensor.

18. The system as claimed in claim 16, wherein the sensor device is configured to detect electrical activity of the patient's heart function.

19. A method for reducing the mean pulmonary venous pressure in a pulmonary vein of a patient comprising:
(a) providing a prosthetic partitioning device coaxially attached on the exterior of the pulmonary vein and movable between a first configuration permitting a less restricted blood flow through the vein and a second configuration permitting a more restricted blood flow through the vein, the transition between the first and second configuration of the device progressing along the length of the coaxially attached pulmonary vein; and
(b) transmitting signals to the prosthetic partitioning device to effectuate the transition from the first configuration to the second configuration whereby assumption of the second configuration restricts blood flow and results in a lowering of mean pulmonary venous pressure.

20. The method as claimed in claim 19, further comprising monitoring physiological characteristics of the patient.

21. The method as claimed in claim 20, wherein the step of monitoring physiological characteristics of the patient comprises monitoring the electrical activity of the patient's heart function.

* * * * *